US010925972B2

(12) United States Patent
Demetriou et al.

(10) Patent No.: US 10,925,972 B2
(45) Date of Patent: Feb. 23, 2021

(54) GLYCAN-DEPENDENT IMMUNOTHERAPEUTIC MOLECULES

(71) Applicant: THE REGENTS OF THE UNIVERSITY OF CALIFORNIA, Oakland, CA (US)

(72) Inventors: Michael Demetriou, Irvine, CA (US); Raymond Wenhou Zhou, Sacramento, CA (US)

(73) Assignee: The Regents of The University of California, Oakland, CA (US)

( * ) Notice: Subject to any disclaimer, the term of this patent is extended or adjusted under 35 U.S.C. 154(b) by 161 days.

(21) Appl. No.: 15/571,101

(22) PCT Filed: Apr. 29, 2016

(86) PCT No.: PCT/US2016/030113
§ 371 (c)(1),
(2) Date: Nov. 1, 2017

(87) PCT Pub. No.: WO2016/178996
PCT Pub. Date: Nov. 10, 2016

(65) Prior Publication Data
US 2018/0169260 A1 Jun. 21, 2018

Related U.S. Application Data

(60) Provisional application No. 62/155,761, filed on May 1, 2015.

(51) Int. Cl.
| | | |
|---|---|---|
| *A61K 47/68* | (2017.01) | |
| *A61K 38/16* | (2006.01) | |
| *C07K 16/28* | (2006.01) | |
| *A61P 35/00* | (2006.01) | |

(52) U.S. Cl.
CPC ........ *A61K 47/6849* (2017.08); *A61K 38/168* (2013.01); *A61P 35/00* (2018.01); *C07K 16/2809* (2013.01); *C07K 16/2851* (2013.01); *C07K 2317/24* (2013.01); *C07K 2317/31* (2013.01); *C07K 2317/622* (2013.01); *C07K 2319/33* (2013.01)

(58) Field of Classification Search
None
See application file for complete search history.

(56) References Cited

U.S. PATENT DOCUMENTS

| 2005/0026866 A1 | 2/2005 | Pawelek |
|---|---|---|
| 2005/0181997 A1 | 8/2005 | Colucci et al. |
| 2006/0148681 A1 | 7/2006 | Lei et al. |
| 2010/0104572 A1 | 4/2010 | Luria |
| 2013/0287748 A1 | 10/2013 | June et al. |
| 2014/0099309 A1 | 4/2014 | Powell, Jr. et al. |
| 2014/0271635 A1 | 9/2014 | Brogdon et al. |
| 2014/0370017 A1 | 12/2014 | June et al. |
| 2015/0110789 A1 | 4/2015 | Liu et al. |
| 2015/0119555 A1 | 4/2015 | Jung et al. |

FOREIGN PATENT DOCUMENTS

| IL | 198479 | 12/2012 |
|---|---|---|
| JP | 2006-514690 A | 5/2006 |
| WO | 2008/053486 A1 | 5/2008 |
| WO | 2011/145085 A2 | 11/2011 |
| WO | 2013/151649 A1 | 10/2013 |
| WO | WO-2013/158856 A2 | 10/2013 |
| WO | WO-2014/031687 A1 | 2/2014 |
| WO | 2015/017734 A1 | 2/2015 |
| WO | 2015/054600 A2 | 4/2015 |
| WO | 2016/057916 A1 | 4/2016 |
| WO | 2016/077526 A1 | 5/2016 |

OTHER PUBLICATIONS

Medeiros et al. (J Nat Med, 67: 247-254, 2013).*
McCarthy et al. (J. Immunol. Methods, 251(1-2): 137-149, 2001).*
Lin et al. (African Journal of Biotechnology, 10(79):18294-18302, 2011).*
Barrett et al., "Chimeric Antigen Receptor Therapy for Cancer," Annu Rev Med. 2014, 65:333-347.
Cazel et al., "Tumour-associated carbohydrate antigens in breast cancer," Breast Cancer Research, 2010, 12:204, pp. 1-13.
Feng et al., "Recent Advance in Tumor-associated Carbohydrate Antigens (TACAs)-based Antitumor Vaccines," ACS Chem. Biol., 2016, 11:850-863.
Hakomori, "Glycosylation defining cancer malignancy: New wine in an old bottle," PNAS, 2002, 99(16):10231-10233.
Kaneda et al., "The High Specificities of Phaseolus vulgaris Erythro- and Leukoagglutinating Lectins for Bisecting GlcNAc or Beta1-6-Linked Branch Structures, Respectively, Are Attributable to Loop B," The Journal of Biological Chemistry, 2002, 277(19):16928-16935.
Kim et al., "Perspectives on the significance of altered glycosylation of glycoproteins in cancer," Glycoconjugate Journal, 1997, 14:569-576.
Schmutz et al., NCBI Reference Sequence: XP_007152772.1, 2014.
Scott et al., "Antibody therapy of cancer," 2012, Nature Reviews, Cancer, 12:278-287.
Singh et al., "Nature of Tumor Control by Permanently and Transiently ModifiedGD2Chimeric Antigen Receptor T Cell in Xenograft Models of Neuroblastoma," Cancer Immunol Res, 2014, 2(11):1059-70.
Staerz et al., "Hybrid antibodies can target sites for attack by T cells," Nature, 1985, 314:628-631.
Westwood et al., "Adoptive transfer of T cells modified with a humanized chimeric receptor gene inhibits growth of Lewis-Y-expressing tumors in mice," PNAS, 2005, 102(52):19051-19056.
Medeiros et al., "A Tn antigen binding lectin from Myrsine coriacea displays toxicity in human cancer cell lines," Journal of Natural Medicines, 2013, 67(2):247-254.

(Continued)

*Primary Examiner* — Nelson B Moseley, II
(74) *Attorney, Agent, or Firm* — Foley & Lardner LLP

(57) ABSTRACT

The present invention relates to compositions and methods for treating cancer. The invention makes use of peptides, nucleic acids encoding such peptides, and cells expressing such peptides, where the peptide comprises a tumor-associated carbohydrate antigen (TACA)-binding domain.

11 Claims, 6 Drawing Sheets
Specification includes a Sequence Listing.

(56) References Cited

OTHER PUBLICATIONS

Cunto-Amesty et al., "Strategies in cancer vaccines development", International Journal for Parasitology, vol. 33, Feb. 11, 2003, pp. 597-613.
Kumaresan et al., "Bioengineering T cells to target carbohydrate to treat opportunistic fungal infection", PNAS, vol. 111, No. 29, Jul. 22, 2014, pp. 10660-10665.
Lu et al., "Targeting Human C-Type Lectin-Like Molecule-1 (CLL1) with a Bispecific Antibody for Immunotherapy of Acute Myeloid Leukemia", Angew. chem. Int. Ed., vol. 53, Jul. 23, 2014, pp. 9841-9845.
Monzavi-Karbassi et al., "Tumor-Associated Glycans and Immune Surveillance", Vaccines, vol. 1, Jun. 17, 2013, pp. 174-203.
Mody et al,. "Use of Lectins as Diagnostic and Therapeutic Tools for Cancer," Journal of Pharmacological and Toxicological Methods, 1995, 33:1-10.
UniProtKB-P24146 (LEC4-GRISI), Lectin-4, Mar. 1, 1992, 6 pages.

\* cited by examiner

```
                         SEQUENCE LISTING

<160> NUMBER OF SEQ ID NOS: 18

<210> SEQ ID NO 1
<211> LENGTH: 252
<212> TYPE: PRT
<213> ORGANISM: Phaseolus vulgaris

<400> SEQUENCE: 1

Ser Asn Asp Ile Tyr Phe Asn Phe Gln Arg Phe Asn Glu Thr Asn Leu
1               5                   10                  15

Ile Leu Gln Arg Asp Ala Ser Val Ser Ser Ser Gly Gln Leu Arg Leu
            20                  25                  30

Thr Asn Leu Asn Gly Asn Gly Glu Pro Arg Val Gly Ser Leu Gly Arg
        35                  40                  45

Ala Phe Tyr Ser Ala Pro Ile Gln Ile Trp Asp Asn Thr Thr Gly Thr
    50                  55                  60

Val Ala Ser Phe Ala Thr Ser Phe Thr Phe Asn Ile Gln Val Pro Asn
65                  70                  75                  80

Asn Ala Gly Pro Ala Asp Gly Leu Ala Phe Ala Leu Val Pro Val Gly
                85                  90                  95

Ser Gln Pro Lys Asp Lys Gly Gly Phe Leu Gly Leu Phe Asp Gly Ser
            100                 105                 110

Asn Ser Asn Phe His Thr Val Ala Val Glu Phe Asp Thr Leu Tyr Asn
        115                 120                 125

Lys Asp Trp Asp Pro Thr Glu Arg His Ile Gly Ile Asp Val Asn Ser
    130                 135                 140

Ile Arg Ser Ile Lys Thr Thr Arg Trp Asp Phe Val Asn Gly Glu Asn
145                 150                 155                 160

Ala Glu Val Leu Ile Thr Tyr Asp Ser Ser Thr Asn Leu Leu Val Ala
                165                 170                 175

Ser Leu Val Tyr Pro Ser Gln Lys Thr Ser Phe Ile Val Ser Asp Thr
            180                 185                 190

Val Asp Leu Lys Ser Val Leu Pro Glu Trp Val Ser Val Gly Phe Ser
        195                 200                 205

Ala Thr Thr Gly Ile Asn Lys Gly Asn Val Glu Thr Asn Asp Val Leu
    210                 215                 220

Ser Trp Ser Phe Ala Ser Lys Leu Ser Asp Gly Thr Thr Ser Glu Gly
225                 230                 235                 240

Leu Asn Leu Ala Asn Leu Val Leu Asn Lys Ile Leu
                245                 250

<210> SEQ ID NO 2
<211> LENGTH: 247
<212> TYPE: PRT
```

<213> ORGANISM: Artificial Sequence
<220> FEATURE:
<223> OTHER INFORMATION: Chemically Synthesized

<400> SEQUENCE: 2

```
Phe Asn Phe Gln Arg Phe Asn Glu Thr Asn Leu Ile Leu Gln Arg Asp
1               5                   10                  15

Ala Ser Val Ser Ser Gly Gln Leu Arg Leu Thr Asn Leu Asn Gly
            20                  25                  30

Asn Gly Glu Pro Arg Val Gly Leu Gly Arg Ala Phe Tyr Ser Ala
        35                  40                  45

Pro Ile Gln Ile Trp Asp Asn Thr Thr Gly Thr Val Ala Ser Phe Ala
50                  55                  60

Thr Ser Phe Thr Phe Asn Ile Gln Val Pro Asn Asn Ala Gly Pro Ala
65                  70                  75                  80

Asp Gly Leu Ala Phe Ala Leu Val Pro Val Gly Ser Gln Pro Lys Asp
                85                  90                  95

Lys Gly Gly Phe Leu Gly Leu Phe Asp Gly Ser Asn Ser Asn Phe His
            100                 105                 110

Thr Val Ala Val Glu Phe Asp Thr Leu Tyr Asn Lys Asp Trp Asp Pro
        115                 120                 125

Thr Glu Arg His Ile Gly Ile Asp Val Asn Ser Ile Arg Ser Ile Lys
130                 135                 140

Thr Thr Arg Trp Asp Phe Val Asn Gly Glu Asn Ala Glu Val Leu Ile
145                 150                 155                 160

Thr Tyr Asp Ser Ser Thr Asn Leu Leu Val Ala Ser Leu Val Tyr Pro
                165                 170                 175

Ser Gln Lys Thr Ser Phe Ile Val Ser Asp Thr Val Asp Leu Lys Ser
            180                 185                 190

Val Leu Pro Glu Trp Val Ser Val Gly Phe Ser Ala Thr Thr Gly Ile
        195                 200                 205

Asn Lys Gly Asn Val Glu Thr Asn Asp Val Leu Ser Trp Ser Phe Ala
210                 215                 220

Ser Lys Leu Ser Asp Gly Thr Thr Ser Glu Gly Leu Asn Leu Ala Asn
225                 230                 235                 240

Leu Val Leu Asn Lys Ile Leu
                245
```

<210> SEQ ID NO 3
<211> LENGTH: 252
<212> TYPE: PRT
<213> ORGANISM: Artificial Sequence
<220> FEATURE:
<223> OTHER INFORMATION: Chemically Synthesized

<400> SEQUENCE: 3

```
Ala Ser Gln Thr Ser Phe Ser Phe Gln Arg Phe Asn Glu Thr Asn Leu
1               5                   10                  15

Ile Leu Gln Arg Asp Ala Thr Val Ser Ser Lys Gly Gln Leu Arg Leu
            20                  25                  30

Thr Asn Val Asn Asp Asn Gly Glu Pro Thr Leu Ser Ser Leu Gly Arg
        35                  40                  45

Ala Phe Tyr Ser Ala Pro Ile Gln Ile Trp Asp Asn Thr Thr Gly Ala
    50                  55                  60

Val Ala Ala Ser Pro Thr Ser Phe Thr Phe Asn Ile Asp Val Pro Asn
65                  70                  75                  80
```

```
Asn Ser Gly Pro Ala Asp Gly Leu Ala Phe Ala Leu Val Pro Val Gly
                85                  90                  95

Ser Gln Pro Lys Asp Lys Gly Phe Leu Gly Leu Phe Asp Gly Ser
            100                 105                 110

Asn Ser Asn Phe His Thr Val Ala Val Glu Phe Asp Thr Leu Tyr Asn
            115                 120                 125

Lys Asp Trp Asp Pro Lys Pro Arg His Ile Gly Ile Asp Val Asn Ser
130                 135                 140

Ile Lys Ser Ile Lys Thr Thr Thr Trp Asp Phe Val Lys Gly Glu Asn
145                 150                 155                 160

Ala Glu Val Leu Ile Thr Tyr Asp Ser Ser Thr Lys Leu Leu Val Ala
                165                 170                 175

Ser Leu Val Tyr Pro Ser Leu Lys Thr Ser Phe Ile Val Ser Asp Thr
                180                 185                 190

Val Asp Leu Lys Ser Val Leu Pro Glu Trp Val Ile Val Gly Phe Thr
            195                 200                 205

Ala Thr Thr Gly Ile Thr Lys Gly Asn Val Glu Thr Asn Asp Ile Leu
            210                 215                 220

Ser Trp Ser Phe Ala Ser Lys Leu Ser Asp Gly Thr Thr Ser Glu Ala
225                 230                 235                 240

Leu Asn Leu Ala Asn Phe Ala Leu Asn Gln Ile Leu
                245                 250

<210> SEQ ID NO 4
<211> LENGTH: 247
<212> TYPE: PRT
<213> ORGANISM: Artificial Sequence
<220> FEATURE:
<223> OTHER INFORMATION: Chemically Synthesized

<400> SEQUENCE: 4

Phe Ser Phe Gln Arg Phe Asn Glu Thr Asn Leu Ile Leu Gln Arg Asp
1               5                   10                  15

Ala Thr Val Ser Ser Lys Gly Gln Leu Arg Leu Thr Asn Val Asn Asp
                20                  25                  30

Asn Gly Glu Pro Thr Leu Ser Ser Leu Gly Arg Ala Phe Tyr Ser Ala
            35                  40                  45

Pro Ile Gln Ile Trp Asp Asn Thr Thr Gly Ala Val Ala Ala Ser Pro
50                  55                  60

Thr Ser Phe Thr Phe Asn Ile Asp Val Pro Asn Asn Ser Gly Pro Ala
65                  70                  75                  80

Asp Gly Leu Ala Phe Ala Leu Val Pro Val Gly Ser Gln Pro Lys Asp
                85                  90                  95

Lys Gly Phe Leu Gly Leu Phe Asp Gly Ser Asn Ser Asn Phe His
            100                 105                 110

Thr Val Ala Val Glu Phe Asp Thr Leu Tyr Asn Lys Asp Trp Asp Pro
            115                 120                 125

Lys Pro Arg His Ile Gly Ile Asp Val Asn Ser Ile Lys Ser Ile Lys
            130                 135                 140

Thr Thr Thr Trp Asp Phe Val Lys Gly Glu Asn Ala Glu Val Leu Ile
145                 150                 155                 160

Thr Tyr Asp Ser Ser Thr Lys Leu Leu Val Ala Ser Leu Val Tyr Pro
                165                 170                 175

Ser Leu Lys Thr Ser Phe Ile Val Ser Asp Thr Val Asp Leu Lys Ser
            180                 185                 190
```

```
Val Leu Pro Glu Trp Val Ile Val Gly Phe Thr Ala Thr Gly Ile
            195                 200                 205

Thr Lys Gly Asn Val Glu Thr Asn Asp Ile Leu Ser Trp Ser Phe Ala
    210                 215                 220

Ser Lys Leu Ser Asp Gly Thr Thr Ser Glu Ala Leu Asn Leu Ala Asn
225                 230                 235                 240

Phe Ala Leu Asn Gln Ile Leu
                245

<210> SEQ ID NO 5
<211> LENGTH: 233
<212> TYPE: PRT
<213> ORGANISM: Vicia villosa

<400> SEQUENCE: 5

Thr Glu Ser Thr Ser Phe Ser Phe Thr Asn Phe Asn Pro Asn Gln Asn
1               5                   10                  15

Asn Leu Ile Leu Gln Glu Asp Ala Leu Val Asn Ser Ala Gly Thr Leu
            20                  25                  30

Glu Leu Thr Ala Val Ala Ala Gly Ala Pro Val Pro Asp Ser Leu Gly
        35                  40                  45

Arg Ala Leu Tyr Ala Ala Pro Ile His Ile His Asp Asn Thr Thr Leu
    50                  55                  60

Ala Ser Phe Thr Thr Ser Phe Ser Phe Val Met Ala Ala Pro Ala Ala
65                  70                  75                  80

Ala Ala Val Ala Asp Gly Leu Ala Phe Phe Leu Ala Pro Pro Asp Thr
                85                  90                  95

Gln Pro Gln Ala Arg Gly Gly Phe Leu Gly Leu Phe Ala Asp Arg Ala
            100                 105                 110

His Asp Ala Ser Tyr Gln Thr Val Ala Val Glu Phe Asp Thr Tyr Ser
        115                 120                 125

Asn Ala Trp Asp Pro Asn Tyr Thr His Ile Gly Ile Asp Thr Asn Gly
    130                 135                 140

Ile Glu Ser Lys Lys Thr Thr Pro Phe Asp Met Val Tyr Gly Glu Lys
145                 150                 155                 160

Ala Asn Ile Val Ile Thr Tyr Gln Ala Ser Thr Lys Ala Leu Ala Ala
                165                 170                 175

Ser Leu Val Phe Pro Val Ser Gln Thr Ser Tyr Ala Val Ser Ala Arg
            180                 185                 190

Val Asp Leu Arg Asp Ile Leu Pro Glu Tyr Val Arg Val Gly Phe Ser
        195                 200                 205

Ala Thr Thr Gly Leu Asn Ala Gly Val Val Glu Thr His Asp Ile Val
    210                 215                 220

Ser Trp Ser Phe Ala Val Ser Leu Ala
225                 230

<210> SEQ ID NO 6
<211> LENGTH: 228
<212> TYPE: PRT
<213> ORGANISM: Artificial Sequence
<220> FEATURE:
<223> OTHER INFORMATION: Chemically synthesized

<400> SEQUENCE: 6

Phe Ser Phe Thr Asn Phe Asn Pro Asn Gln Asn Asn Leu Ile Leu Gln
1               5                   10                  15

Glu Asp Ala Leu Val Asn Ser Ala Gly Thr Leu Glu Leu Thr Ala Val
```

```
                    20                  25                  30
Ala Ala Gly Ala Pro Val Pro Asp Ser Leu Gly Arg Ala Leu Tyr Ala
            35                  40                  45
Ala Pro Ile His Ile His Asp Asn Thr Thr Leu Ala Ser Phe Thr Thr
 50                  55                  60
Ser Phe Ser Phe Val Met Ala Ala Pro Ala Ala Ala Val Ala Asp
 65                  70                  75                  80
Gly Leu Ala Phe Phe Leu Ala Pro Pro Asp Thr Gln Pro Gln Ala Arg
                    85                  90                  95
Gly Gly Phe Leu Gly Leu Phe Ala Asp Arg Ala His Asp Ala Ser Tyr
            100                 105                 110
Gln Thr Val Ala Val Glu Phe Asp Thr Tyr Ser Asn Ala Trp Asp Pro
            115                 120                 125
Asn Tyr Thr His Ile Gly Ile Asp Thr Asn Gly Ile Glu Ser Lys Lys
            130                 135                 140
Thr Thr Pro Phe Asp Met Val Tyr Gly Glu Lys Ala Asn Ile Val Ile
145                 150                 155                 160
Thr Tyr Gln Ala Ser Thr Lys Ala Leu Ala Ala Ser Leu Val Phe Pro
                165                 170                 175
Val Ser Gln Thr Ser Tyr Ala Val Ser Ala Arg Val Asp Leu Arg Asp
                180                 185                 190
Ile Leu Pro Glu Tyr Val Arg Val Gly Phe Ser Ala Thr Thr Gly Leu
            195                 200                 205
Asn Ala Gly Val Val Glu Thr His Asp Ile Val Ser Trp Ser Phe Ala
            210                 215                 220
Val Ser Leu Ala
225

<210> SEQ ID NO 7
<211> LENGTH: 256
<212> TYPE: PRT
<213> ORGANISM: Artificial Sequence
<220> FEATURE:
<223> OTHER INFORMATION: Chemically Synthesized

<400> SEQUENCE: 7

Gln Asn Ser Lys Phe Gln Arg Asp Leu Val Thr Leu Arg Thr Asp Phe
 1               5                  10                  15
Ser Asn Phe Thr Ser Asn Thr Val Ala Glu Ile Gln Ala Leu Thr Ser
                20                  25                  30
Gln Gly Ser Ser Leu Glu Glu Thr Ile Ala Ser Leu Lys Ala Glu Val
            35                  40                  45
Glu Gly Phe Lys Gln Glu Arg Gln Ala Gly Val Ser Glu Leu Gln Glu
        50                  55                  60
His Thr Thr Gln Lys Ala His Leu Gly His Cys Pro His Cys Pro Ser
 65                  70                  75                  80
Val Cys Val Pro Val His Ser Glu Met Leu Leu Arg Val Gln Gln Leu
                85                  90                  95
Val Gln Asp Leu Lys Lys Leu Thr Cys Gln Val Ala Thr Leu Asn Asn
            100                 105                 110
Asn Ala Ser Thr Glu Gly Thr Cys Cys Pro Val Asn Trp Val Glu His
            115                 120                 125
Gln Asp Ser Cys Tyr Trp Phe Ser His Ser Gly Met Ser Trp Ala Glu
            130                 135                 140
Ala Glu Lys Tyr Cys Gln Leu Lys Asn Ala His Leu Val Val Ile Asn
```

```
                145                 150                 155                 160
Ser Arg Glu Glu Gln Asn Phe Val Gln Lys Tyr Leu Gly Ser Ala Tyr
                    165                 170                 175

Thr Trp Met Gly Leu Ser Asp Pro Glu Gly Ala Trp Lys Trp Val Asp
                    180                 185                 190

Gly Thr Asp Tyr Ala Thr Gly Phe Gln Asn Trp Lys Pro Gly Gln Pro
                    195                 200                 205

Asp Asp Trp Gln Gly His Gly Leu Gly Gly Glu Asp Cys Ala His
            210                 215                 220

Phe His Pro Asp Gly Arg Trp Asn Asp Val Cys Gln Arg Pro Tyr
225                 230                 235                 240

His Trp Val Cys Glu Ala Gly Leu Gly Gln Thr Ser Gln Glu Ser His
                    245                 250                 255

<210> SEQ ID NO 8
<211> LENGTH: 19
<212> TYPE: PRT
<213> ORGANISM: Artificial Sequence
<220> FEATURE:
<223> OTHER INFORMATION: Chemically Synthesized

<400> SEQUENCE: 8

Met Gly Trp Ser Cys Ile Ile Leu Phe Leu Val Ala Thr Ala Thr Gly
1               5                   10                  15

Val His Ser

<210> SEQ ID NO 9
<211> LENGTH: 243
<212> TYPE: PRT
<213> ORGANISM: Artificial Sequence
<220> FEATURE:
<223> OTHER INFORMATION: Chemically Synthesized

<400> SEQUENCE: 9

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
                100                 105                 110

Thr Thr Leu Thr Val Ser Val Glu Gly Gly Ser Gly Gly Ser Gly
            115                 120                 125

Gly Ser Gly Gly Ser Gly Gly Val Asp Asp Ile Gln Leu Thr Gln Ser
        130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
```

```
                    180                 185                 190
Gly Val Pro Tyr Arg Phe Ser Gly Ser Gly Ser Gly Thr Ser Tyr Ser
                195                 200                 205

Leu Thr Ile Ser Ser Met Glu Ala Glu Asp Ala Ala Thr Tyr Tyr Cys
        210                 215                 220

Gln Gln Trp Ser Ser Asn Pro Leu Thr Phe Gly Ala Gly Thr Lys Leu
225                 230                 235                 240

Glu Leu Lys

<210> SEQ ID NO 10
<211> LENGTH: 5
<212> TYPE: PRT
<213> ORGANISM: Artificial Sequence
<220> FEATURE:
<223> OTHER INFORMATION: Chemically Synthesized

<400> SEQUENCE: 10

Gly Gly Gly Gly Ser
1               5

<210> SEQ ID NO 11
<211> LENGTH: 525
<212> TYPE: PRT
<213> ORGANISM: Artificial Sequence
<220> FEATURE:
<223> OTHER INFORMATION: Chemically Synthesized

<400> SEQUENCE: 11

Met Gly Trp Ser Cys Ile Ile Leu Phe Leu Val Ala Thr Ala Thr Gly
1               5                   10                  15

Val His Ser Ser Asn Asp Ile Tyr Phe Asn Phe Gln Arg Phe Asn Glu
                20                  25                  30

Thr Asn Leu Ile Leu Gln Arg Asp Ala Ser Val Ser Ser Ser Gly Gln
            35                  40                  45

Leu Arg Leu Thr Asn Leu Asn Gly Asn Gly Glu Pro Arg Val Gly Ser
        50                  55                  60

Leu Gly Arg Ala Phe Tyr Ser Ala Pro Ile Gln Ile Trp Asp Asn Thr
65                  70                  75                  80

Thr Gly Thr Val Ala Ser Phe Ala Thr Ser Phe Thr Phe Asn Ile Gln
                85                  90                  95

Val Pro Asn Asn Ala Gly Pro Ala Asp Gly Leu Ala Phe Ala Leu Val
            100                 105                 110

Pro Val Gly Ser Gln Pro Lys Asp Lys Gly Gly Phe Leu Gly Leu Phe
        115                 120                 125

Asp Gly Ser Asn Ser Asn Phe His Thr Val Ala Val Glu Phe Asp Thr
130                 135                 140

Leu Tyr Asn Lys Asp Trp Asp Pro Thr Glu Arg His Ile Gly Ile Asp
145                 150                 155                 160

Val Asn Ser Ile Arg Ser Ile Lys Thr Thr Arg Trp Asp Phe Val Asn
                165                 170                 175

Gly Glu Asn Ala Glu Val Leu Ile Thr Tyr Asp Ser Ser Thr Asn Leu
            180                 185                 190

Leu Val Ala Ser Leu Val Tyr Pro Ser Gln Lys Thr Ser Phe Ile Val
        195                 200                 205

Ser Asp Thr Val Asp Leu Lys Ser Val Leu Pro Glu Trp Val Ser Val
    210                 215                 220

Gly Phe Ser Ala Thr Thr Gly Ile Asn Lys Gly Asn Val Glu Thr Asn
```

```
                225                 230                 235                 240
Asp Val Leu Ser Trp Ser Phe Ala Ser Lys Leu Ser Asp Gly Thr Thr
                    245                 250                 255

Ser Glu Gly Leu Asn Leu Ala Asn Leu Val Leu Asn Lys Ile Leu Gly
                260                 265                 270

Gly Gly Gly Ser Asp Ile Lys Leu Gln Gln Ser Gly Ala Glu Leu Ala
                275                 280                 285

Arg Pro Gly Ala Ser Val Lys Met Ser Cys Lys Thr Ser Gly Tyr Thr
290                 295                 300

Phe Thr Arg Tyr Thr Met His Trp Val Lys Gln Arg Pro Gly Gln Gly
305                 310                 315                 320

Leu Glu Trp Ile Gly Tyr Ile Asn Pro Ser Arg Gly Tyr Thr Asn Tyr
                325                 330                 335

Asn Gln Lys Phe Lys Asp Lys Ala Thr Leu Thr Thr Asp Lys Ser Ser
                340                 345                 350

Ser Thr Ala Tyr Met Gln Leu Ser Ser Leu Thr Ser Glu Asp Ser Ala
                355                 360                 365

Val Tyr Tyr Cys Ala Arg Tyr Tyr Asp Asp His Tyr Cys Leu Asp Tyr
            370                 375                 380

Trp Gly Gln Gly Thr Thr Leu Thr Val Ser Ser Val Glu Gly Gly Ser
385                 390                 395                 400

Gly Gly Ser Gly Gly Ser Gly Gly Ser Gly Gly Val Asp Asp Ile Gln
                405                 410                 415

Leu Thr Gln Ser Pro Ala Ile Met Ser Ala Ser Pro Gly Glu Lys Val
                420                 425                 430

Thr Met Thr Cys Arg Ala Ser Ser Ser Val Ser Tyr Met Asn Trp Tyr
            435                 440                 445

Gln Gln Lys Ser Gly Thr Ser Pro Lys Arg Trp Ile Tyr Asp Thr Ser
        450                 455                 460

Lys Val Ala Ser Gly Val Pro Tyr Arg Phe Ser Gly Ser Gly Ser Gly
465                 470                 475                 480

Thr Ser Tyr Ser Leu Thr Ile Ser Ser Met Glu Ala Glu Asp Ala Ala
                485                 490                 495

Thr Tyr Tyr Cys Gln Gln Trp Ser Ser Asn Pro Leu Thr Phe Gly Ala
            500                 505                 510

Gly Thr Lys Leu Glu Leu Lys His His His His His
        515                 520                 525

<210> SEQ ID NO 12
<211> LENGTH: 520
<212> TYPE: PRT
<213> ORGANISM: Artificial Sequence
<220> FEATURE:
<223> OTHER INFORMATION: Chemically Synthesized

<400> SEQUENCE: 12

Met Gly Trp Ser Cys Ile Ile Leu Phe Leu Val Ala Thr Ala Thr Gly
1                   5                   10                  15

Val His Ser Phe Asn Phe Gln Arg Phe Asn Glu Thr Asn Leu Ile Leu
                20                  25                  30

Gln Arg Asp Ala Ser Val Ser Ser Gly Gln Leu Arg Leu Thr Asn
            35                  40                  45

Leu Asn Gly Asn Gly Glu Pro Arg Val Gly Ser Leu Gly Arg Ala Phe
        50                  55                  60

Tyr Ser Ala Pro Ile Gln Ile Trp Asp Asn Thr Thr Gly Thr Val Ala
```

-continued

```
                65                  70                  75                  80
Ser Phe Ala Thr Ser Phe Thr Phe Asn Ile Gln Val Pro Asn Asn Ala
                    85                  90                  95
Gly Pro Ala Asp Gly Leu Ala Phe Ala Leu Val Pro Val Gly Ser Gln
                    100                 105                 110
Pro Lys Asp Lys Gly Gly Phe Leu Gly Leu Phe Asp Gly Ser Asn Ser
                    115                 120                 125
Asn Phe His Thr Val Ala Val Glu Phe Asp Thr Leu Tyr Asn Lys Asp
                    130                 135                 140
Trp Asp Pro Thr Glu Arg His Ile Gly Ile Asp Val Asn Ser Ile Arg
145                 150                 155                 160
Ser Ile Lys Thr Thr Arg Trp Asp Phe Val Asn Gly Glu Asn Ala Glu
                    165                 170                 175
Val Leu Ile Thr Tyr Asp Ser Ser Thr Asn Leu Leu Val Ala Ser Leu
                    180                 185                 190
Val Tyr Pro Ser Gln Lys Thr Ser Phe Ile Val Ser Asp Thr Val Asp
                    195                 200                 205
Leu Lys Ser Val Leu Pro Glu Trp Val Ser Val Gly Phe Ser Ala Thr
                    210                 215                 220
Thr Gly Ile Asn Lys Gly Asn Val Glu Thr Asn Asp Val Leu Ser Trp
225                 230                 235                 240
Ser Phe Ala Ser Lys Leu Ser Asp Gly Thr Thr Ser Glu Gly Leu Asn
                    245                 250                 255
Leu Ala Asn Leu Val Leu Asn Lys Ile Leu Gly Gly Gly Ser Asp
                    260                 265                 270
Ile Lys Leu Gln Gln Ser Gly Ala Glu Leu Ala Arg Pro Gly Ala Ser
                    275                 280                 285
Val Lys Met Ser Cys Lys Thr Ser Gly Tyr Thr Phe Thr Arg Tyr Thr
                    290                 295                 300
Met His Trp Val Lys Gln Arg Pro Gly Gln Gly Leu Glu Trp Ile Gly
305                 310                 315                 320
Tyr Ile Asn Pro Ser Arg Gly Tyr Thr Asn Tyr Asn Gln Lys Phe Lys
                    325                 330                 335
Asp Lys Ala Thr Leu Thr Thr Asp Lys Ser Ser Ser Thr Ala Tyr Met
                    340                 345                 350
Gln Leu Ser Ser Leu Thr Ser Glu Asp Ser Ala Val Tyr Tyr Cys Ala
                    355                 360                 365
Arg Tyr Tyr Asp Asp His Tyr Cys Leu Asp Tyr Trp Gly Gln Gly Thr
                    370                 375                 380
Thr Leu Thr Val Ser Ser Val Glu Gly Gly Ser Gly Gly Ser Gly Gly
385                 390                 395                 400
Ser Gly Gly Ser Gly Gly Val Asp Asp Ile Gln Leu Thr Gln Ser Pro
                    405                 410                 415
Ala Ile Met Ser Ala Ser Pro Gly Glu Lys Val Thr Met Thr Cys Arg
                    420                 425                 430
Ala Ser Ser Ser Val Ser Tyr Met Asn Trp Tyr Gln Gln Lys Ser Gly
                    435                 440                 445
Thr Ser Pro Lys Arg Trp Ile Tyr Asp Thr Ser Lys Val Ala Ser Gly
                    450                 455                 460
Val Pro Tyr Arg Phe Ser Gly Ser Gly Ser Gly Thr Ser Tyr Ser Leu
465                 470                 475                 480
Thr Ile Ser Ser Met Glu Ala Glu Asp Ala Ala Thr Tyr Tyr Cys Gln
                    485                 490                 495
```

-continued

Gln Trp Ser Ser Asn Pro Leu Thr Phe Gly Ala Gly Thr Lys Leu Glu
            500                 505                 510

Leu Lys His His His His His
        515             520

<210> SEQ ID NO 13
<211> LENGTH: 525
<212> TYPE: PRT
<213> ORGANISM: Artificial Sequence
<220> FEATURE:
<223> OTHER INFORMATION: Chemically Synthesized

<400> SEQUENCE: 13

Met Gly Trp Ser Cys Ile Ile Leu Phe Leu Val Ala Thr Ala Thr Gly
1               5                   10                  15

Val His Ser Ala Ser Gln Thr Ser Phe Ser Phe Gln Arg Phe Asn Glu
            20                  25                  30

Thr Asn Leu Ile Leu Gln Arg Asp Ala Thr Val Ser Ser Lys Gly Gln
        35                  40                  45

Leu Arg Leu Thr Asn Val Asn Asp Asn Gly Glu Pro Thr Leu Ser Ser
50                  55                  60

Leu Gly Arg Ala Phe Tyr Ser Ala Pro Ile Gln Ile Trp Asp Asn Thr
65                  70                  75                  80

Thr Gly Ala Val Ala Ser Pro Thr Ser Phe Thr Phe Asn Ile Asp
            85                  90                  95

Val Pro Asn Asn Ser Gly Pro Ala Asp Gly Leu Ala Phe Ala Leu Val
            100                 105                 110

Pro Val Gly Ser Gln Pro Lys Asp Lys Gly Gly Phe Leu Gly Leu Phe
        115                 120                 125

Asp Gly Ser Asn Ser Asn Phe His Thr Val Ala Val Glu Phe Asp Thr
130                 135                 140

Leu Tyr Asn Lys Asp Trp Asp Pro Lys Pro Arg His Ile Gly Ile Asp
145                 150                 155                 160

Val Asn Ser Ile Lys Ser Ile Lys Thr Thr Thr Trp Asp Phe Val Lys
                165                 170                 175

Gly Glu Asn Ala Glu Val Leu Ile Thr Tyr Asp Ser Ser Thr Lys Leu
            180                 185                 190

Leu Val Ala Ser Leu Val Tyr Pro Ser Leu Lys Thr Ser Phe Ile Val
        195                 200                 205

Ser Asp Thr Val Asp Leu Lys Ser Val Leu Pro Glu Trp Val Ile Val
210                 215                 220

Gly Phe Thr Ala Thr Thr Gly Ile Thr Lys Gly Asn Val Glu Thr Asn
225                 230                 235                 240

Asp Ile Leu Ser Trp Ser Phe Ala Ser Lys Leu Ser Asp Gly Thr Thr
                245                 250                 255

Ser Glu Ala Leu Asn Leu Ala Asn Phe Ala Leu Asn Gln Ile Leu Gly
            260                 265                 270

Gly Gly Gly Ser Asp Ile Lys Leu Gln Gln Ser Gly Ala Glu Leu Ala
        275                 280                 285

Arg Pro Gly Ala Ser Val Lys Met Ser Cys Lys Thr Ser Gly Tyr Thr
290                 295                 300

Phe Thr Arg Tyr Thr Met His Trp Val Lys Gln Arg Pro Gly Gln Gly
305                 310                 315                 320

Leu Glu Trp Ile Gly Tyr Ile Asn Pro Ser Arg Gly Tyr Thr Asn Tyr
                325                 330                 335

```
Asn Gln Lys Phe Lys Asp Lys Ala Thr Leu Thr Thr Asp Lys Ser Ser
                340                 345                 350

Ser Thr Ala Tyr Met Gln Leu Ser Ser Leu Thr Ser Glu Asp Ser Ala
            355                 360                 365

Val Tyr Tyr Cys Ala Arg Tyr Tyr Asp Asp His Tyr Cys Leu Asp Tyr
370                 375                 380

Trp Gly Gln Gly Thr Thr Leu Thr Val Ser Ser Val Glu Gly Gly Ser
385                 390                 395                 400

Gly Gly Ser Gly Gly Ser Gly Gly Ser Gly Gly Val Asp Asp Ile Gln
                405                 410                 415

Leu Thr Gln Ser Pro Ala Ile Met Ser Ala Ser Pro Gly Glu Lys Val
            420                 425                 430

Thr Met Thr Cys Arg Ala Ser Ser Ser Val Ser Tyr Met Asn Trp Tyr
        435                 440                 445

Gln Gln Lys Ser Gly Thr Ser Pro Lys Arg Trp Ile Tyr Asp Thr Ser
    450                 455                 460

Lys Val Ala Ser Gly Val Pro Tyr Arg Phe Ser Gly Ser Gly Ser Gly
465                 470                 475                 480

Thr Ser Tyr Ser Leu Thr Ile Ser Ser Met Glu Ala Glu Asp Ala Ala
                485                 490                 495

Thr Tyr Tyr Cys Gln Gln Trp Ser Ser Asn Pro Leu Thr Phe Gly Ala
            500                 505                 510

Gly Thr Lys Leu Glu Leu Lys His His His His His His
            515                 520                 525

<210> SEQ ID NO 14
<211> LENGTH: 520
<212> TYPE: PRT
<213> ORGANISM: Artificial Sequence
<220> FEATURE:
<223> OTHER INFORMATION: Chemically Synthesized

<400> SEQUENCE: 14

Met Gly Trp Ser Cys Ile Ile Leu Phe Leu Val Ala Thr Ala Thr Gly
1               5                   10                  15

Val His Ser Phe Ser Phe Gln Arg Phe Asn Glu Thr Asn Leu Ile Leu
            20                  25                  30

Gln Arg Asp Ala Thr Val Ser Ser Lys Gly Gln Leu Arg Leu Thr Asn
        35                  40                  45

Val Asn Asp Asn Gly Glu Pro Thr Leu Ser Ser Leu Gly Arg Ala Phe
50                  55                  60

Tyr Ser Ala Pro Ile Gln Ile Trp Asp Asn Thr Thr Gly Ala Val Ala
65                  70                  75                  80

Ala Ser Pro Thr Ser Phe Thr Phe Asn Ile Asp Val Pro Asn Asn Ser
                85                  90                  95

Gly Pro Ala Asp Gly Leu Ala Phe Ala Leu Val Pro Val Gly Ser Gln
            100                 105                 110

Pro Lys Asp Lys Gly Gly Phe Leu Gly Leu Phe Asp Gly Ser Asn Ser
        115                 120                 125

Asn Phe His Thr Val Ala Val Glu Phe Asp Thr Leu Tyr Asn Lys Asp
    130                 135                 140

Trp Asp Pro Lys Pro Arg His Ile Gly Ile Asp Val Asn Ser Ile Lys
145                 150                 155                 160

Ser Ile Lys Thr Thr Thr Trp Asp Phe Val Lys Gly Glu Asn Ala Glu
                165                 170                 175
```

Val Leu Ile Thr Tyr Asp Ser Ser Thr Lys Leu Leu Val Ala Ser Leu
            180                 185                 190

Val Tyr Pro Ser Leu Lys Thr Ser Phe Ile Val Ser Asp Thr Val Asp
        195                 200                 205

Leu Lys Ser Val Leu Pro Glu Trp Val Ile Val Gly Phe Thr Ala Thr
    210                 215                 220

Thr Gly Ile Thr Lys Gly Asn Val Glu Thr Asn Asp Ile Leu Ser Trp
225                 230                 235                 240

Ser Phe Ala Ser Lys Leu Ser Asp Gly Thr Thr Ser Glu Ala Leu Asn
                245                 250                 255

Leu Ala Asn Phe Ala Leu Asn Gln Ile Leu Gly Gly Gly Ser Asp
            260                 265                 270

Ile Lys Leu Gln Gln Ser Gly Ala Glu Leu Ala Arg Pro Gly Ala Ser
            275                 280                 285

Val Lys Met Ser Cys Lys Thr Ser Gly Tyr Thr Phe Thr Arg Tyr Thr
        290                 295                 300

Met His Trp Val Lys Gln Arg Pro Gly Gln Gly Leu Glu Trp Ile Gly
305                 310                 315                 320

Tyr Ile Asn Pro Ser Arg Gly Tyr Thr Asn Tyr Asn Gln Lys Phe Lys
                325                 330                 335

Asp Lys Ala Thr Leu Thr Thr Asp Lys Ser Ser Ser Thr Ala Tyr Met
            340                 345                 350

Gln Leu Ser Ser Leu Thr Ser Glu Asp Ser Ala Val Tyr Tyr Cys Ala
        355                 360                 365

Arg Tyr Tyr Asp Asp His Tyr Cys Leu Asp Tyr Trp Gly Gln Gly Thr
    370                 375                 380

Thr Leu Thr Val Ser Ser Val Glu Gly Gly Ser Gly Gly Ser Gly Gly
385                 390                 395                 400

Ser Gly Gly Ser Gly Gly Val Asp Asp Ile Gln Leu Thr Gln Ser Pro
                405                 410                 415

Ala Ile Met Ser Ala Ser Pro Gly Glu Lys Val Thr Met Thr Cys Arg
            420                 425                 430

Ala Ser Ser Ser Val Ser Tyr Met Asn Trp Tyr Gln Gln Lys Ser Gly
        435                 440                 445

Thr Ser Pro Lys Arg Trp Ile Tyr Asp Thr Ser Lys Val Ala Ser Gly
    450                 455                 460

Val Pro Tyr Arg Phe Ser Gly Ser Gly Ser Gly Thr Ser Tyr Ser Leu
465                 470                 475                 480

Thr Ile Ser Ser Met Glu Ala Glu Asp Ala Ala Thr Tyr Tyr Cys Gln
                485                 490                 495

Gln Trp Ser Ser Asn Pro Leu Thr Phe Gly Ala Gly Thr Lys Leu Glu
            500                 505                 510

Leu Lys His His His His His His
        515                 520

<210> SEQ ID NO 15
<211> LENGTH: 487
<212> TYPE: PRT
<213> ORGANISM: Artificial Sequence
<220> FEATURE:
<223> OTHER INFORMATION: Chemically Synthesized

<400> SEQUENCE: 15

Thr Glu Ser Thr Ser Phe Ser Phe Thr Asn Phe Asn Pro Asn Gln Asn
1               5                   10                  15

```
Asn Leu Ile Leu Gln Glu Asp Ala Leu Val Asn Ser Ala Gly Thr Leu
            20                  25                  30

Glu Leu Thr Ala Val Ala Ala Gly Ala Pro Val Pro Asp Ser Leu Gly
        35                  40                  45

Arg Ala Leu Tyr Ala Ala Pro Ile His Ile His Asp Asn Thr Thr Leu
 50                  55                  60

Ala Ser Phe Thr Thr Ser Phe Ser Phe Val Met Ala Ala Pro Ala Ala
 65                  70                  75                  80

Ala Ala Val Ala Asp Gly Leu Ala Phe Phe Leu Ala Pro Pro Asp Thr
                 85                  90                  95

Gln Pro Gln Ala Arg Gly Gly Phe Leu Gly Leu Phe Ala Asp Arg Ala
                100                 105                 110

His Asp Ala Ser Tyr Gln Thr Val Ala Val Glu Phe Asp Thr Tyr Ser
            115                 120                 125

Asn Ala Trp Asp Pro Asn Tyr Thr His Ile Gly Ile Asp Thr Asn Gly
130                 135                 140

Ile Glu Ser Lys Lys Thr Thr Pro Phe Asp Met Val Tyr Gly Glu Lys
145                 150                 155                 160

Ala Asn Ile Val Ile Thr Tyr Gln Ala Ser Thr Lys Ala Leu Ala Ala
                165                 170                 175

Ser Leu Val Phe Pro Val Ser Gln Thr Ser Tyr Ala Val Ser Ala Arg
            180                 185                 190

Val Asp Leu Arg Asp Ile Leu Pro Glu Tyr Val Arg Val Gly Phe Ser
        195                 200                 205

Ala Thr Thr Gly Leu Asn Ala Gly Val Val Glu Thr His Asp Ile Val
    210                 215                 220

Ser Trp Ser Phe Ala Val Ser Leu Ala Gly Gly Gly Ser Asp Ile
225                 230                 235                 240

Lys Leu Gln Gln Ser Gly Ala Glu Leu Ala Arg Pro Gly Ala Ser Val
                245                 250                 255

Lys Met Ser Cys Lys Thr Ser Gly Tyr Thr Phe Thr Arg Tyr Thr Met
            260                 265                 270

His Trp Val Lys Gln Arg Pro Gly Gln Gly Leu Glu Trp Ile Gly Tyr
        275                 280                 285

Ile Asn Pro Ser Arg Gly Tyr Thr Asn Tyr Asn Gln Lys Phe Lys Asp
    290                 295                 300

Lys Ala Thr Leu Thr Thr Asp Lys Ser Ser Ser Thr Ala Tyr Met Gln
305                 310                 315                 320

Leu Ser Ser Leu Thr Ser Glu Asp Ser Ala Val Tyr Tyr Cys Ala Arg
                325                 330                 335

Tyr Tyr Asp Asp His Tyr Cys Leu Asp Tyr Trp Gly Gln Gly Thr Thr
            340                 345                 350

Leu Thr Val Ser Ser Val Glu Gly Gly Ser Gly Gly Ser Gly Gly Ser
        355                 360                 365

Gly Gly Ser Gly Gly Val Asp Asp Ile Gln Leu Thr Gln Ser Pro Ala
    370                 375                 380

Ile Met Ser Ala Ser Pro Gly Glu Lys Val Thr Met Thr Cys Arg Ala
385                 390                 395                 400

Ser Ser Ser Val Ser Tyr Met Asn Trp Tyr Gln Gln Lys Ser Gly Thr
                405                 410                 415

Ser Pro Lys Arg Trp Ile Tyr Asp Thr Ser Lys Val Ala Ser Gly Val
            420                 425                 430
```

Pro Tyr Arg Phe Ser Gly Ser Gly Ser Gly Thr Ser Tyr Ser Leu Thr
            435                 440                 445

Ile Ser Ser Met Glu Ala Glu Asp Ala Ala Thr Tyr Tyr Cys Gln Gln
        450                 455                 460

Trp Ser Ser Asn Pro Leu Thr Phe Gly Ala Gly Thr Lys Leu Glu Leu
465                 470                 475                 480

Lys His His His His His
            485

<210> SEQ ID NO 16
<211> LENGTH: 482
<212> TYPE: PRT
<213> ORGANISM: Artificial Sequence
<220> FEATURE:
<223> OTHER INFORMATION: Chemically Synthesized

<400> SEQUENCE: 16

Phe Ser Phe Thr Asn Phe Asn Pro Asn Gln Asn Asn Leu Ile Leu Gln
1               5                   10                  15

Glu Asp Ala Leu Val Asn Ser Ala Gly Thr Leu Glu Leu Thr Ala Val
            20                  25                  30

Ala Ala Gly Ala Pro Val Pro Asp Ser Leu Gly Arg Ala Leu Tyr Ala
        35                  40                  45

Ala Pro Ile His Ile His Asp Asn Thr Thr Leu Ala Ser Phe Thr Thr
    50                  55                  60

Ser Phe Ser Phe Val Met Ala Ala Pro Ala Ala Ala Val Ala Asp
65                  70                  75                  80

Gly Leu Ala Phe Phe Leu Ala Pro Pro Asp Thr Gln Pro Gln Ala Arg
                85                  90                  95

Gly Gly Phe Leu Gly Leu Phe Ala Asp Arg Ala His Asp Ala Ser Tyr
            100                 105                 110

Gln Thr Val Ala Val Glu Phe Asp Thr Tyr Ser Asn Ala Trp Asp Pro
        115                 120                 125

Asn Tyr Thr His Ile Gly Ile Asp Thr Asn Gly Ile Glu Ser Lys Lys
    130                 135                 140

Thr Thr Pro Phe Asp Met Val Tyr Gly Glu Lys Ala Asn Ile Val Ile
145                 150                 155                 160

Thr Tyr Gln Ala Ser Thr Lys Ala Leu Ala Ala Ser Leu Val Phe Pro
                165                 170                 175

Val Ser Gln Thr Ser Tyr Ala Val Ser Ala Arg Val Asp Leu Arg Asp
            180                 185                 190

Ile Leu Pro Glu Tyr Val Arg Val Gly Phe Ser Ala Thr Thr Gly Leu
        195                 200                 205

Asn Ala Gly Val Val Glu Thr His Asp Ile Val Ser Trp Ser Phe Ala
    210                 215                 220

Val Ser Leu Ala Gly Gly Gly Ser Asp Ile Lys Leu Gln Gln Ser
225                 230                 235                 240

Gly Ala Glu Leu Ala Arg Pro Gly Ala Ser Val Lys Met Ser Cys Lys
                245                 250                 255

Thr Ser Gly Tyr Thr Phe Thr Arg Tyr Thr Met His Trp Val Lys Gln
            260                 265                 270

Arg Pro Gly Gln Gly Leu Glu Trp Ile Gly Tyr Ile Asn Pro Ser Arg
        275                 280                 285

Gly Tyr Thr Asn Tyr Asn Gln Lys Phe Lys Asp Lys Ala Thr Leu Thr
    290                 295                 300

-continued

Thr Asp Lys Ser Ser Ser Thr Ala Tyr Met Gln Leu Ser Ser Leu Thr
305                 310                 315                 320

Ser Glu Asp Ser Ala Val Tyr Tyr Cys Ala Arg Tyr Tyr Asp Asp His
            325                 330                 335

Tyr Cys Leu Asp Tyr Trp Gly Gln Gly Thr Thr Leu Thr Val Ser Ser
        340                 345                 350

Val Glu Gly Gly Ser Gly Gly Ser Gly Gly Ser Gly Gly
    355                 360                 365

Val Asp Asp Ile Gln Leu Thr Gln Ser Pro Ala Ile Met Ser Ala Ser
    370                 375                 380

Pro Gly Glu Lys Val Thr Met Thr Cys Arg Ala Ser Ser Ser Val Ser
385                 390                 395                 400

Tyr Met Asn Trp Tyr Gln Gln Lys Ser Gly Thr Ser Pro Lys Arg Trp
                405                 410                 415

Ile Tyr Asp Thr Ser Lys Val Ala Ser Gly Val Pro Tyr Arg Phe Ser
                420                 425                 430

Gly Ser Gly Ser Gly Thr Ser Tyr Ser Leu Thr Ile Ser Ser Met Glu
        435                 440                 445

Ala Glu Asp Ala Ala Thr Tyr Tyr Cys Gln Gln Trp Ser Ser Asn Pro
450                 455                 460

Leu Thr Phe Gly Ala Gly Thr Lys Leu Glu Leu Lys His His His His
465                 470                 475                 480

His His

<210> SEQ ID NO 17
<211> LENGTH: 510
<212> TYPE: PRT
<213> ORGANISM: Artificial Sequence
<220> FEATURE:
<223> OTHER INFORMATION: Chemically Synthesized

<400> SEQUENCE: 17

Gln Asn Ser Lys Phe Gln Arg Asp Leu Val Thr Leu Arg Thr Asp Phe
1               5                   10                  15

Ser Asn Phe Thr Ser Asn Thr Val Ala Glu Ile Gln Ala Leu Thr Ser
                20                  25                  30

Gln Gly Ser Ser Leu Glu Glu Thr Ile Ala Ser Leu Lys Ala Glu Val
            35                  40                  45

Glu Gly Phe Lys Gln Glu Arg Gln Ala Gly Val Ser Glu Leu Gln Glu
        50                  55                  60

His Thr Thr Gln Lys Ala His Leu Gly His Cys Pro His Cys Pro Ser
65                  70                  75                  80

Val Cys Val Pro Val His Ser Glu Met Leu Leu Arg Val Gln Gln Leu
                85                  90                  95

Val Gln Asp Leu Lys Lys Leu Thr Cys Gln Val Ala Thr Leu Asn Asn
                100                 105                 110

Asn Ala Ser Thr Glu Gly Thr Cys Cys Pro Val Asn Trp Val Glu His
            115                 120                 125

Gln Asp Ser Cys Tyr Trp Phe Ser His Ser Gly Met Ser Trp Ala Glu
        130                 135                 140

Ala Glu Lys Tyr Cys Gln Leu Lys Asn Ala His Leu Val Val Ile Asn
145                 150                 155                 160

Ser Arg Glu Glu Gln Asn Phe Val Gln Lys Tyr Leu Gly Ser Ala Tyr
                165                 170                 175

Thr Trp Met Gly Leu Ser Asp Pro Glu Gly Ala Trp Lys Trp Val Asp

```
            180                 185                 190
Gly Thr Asp Tyr Ala Thr Gly Phe Gln Asn Trp Lys Pro Gly Gln Pro
                195                 200                 205

Asp Asp Trp Gln Gly His Gly Leu Gly Gly Glu Asp Cys Ala His
        210                 215                 220

Phe His Pro Asp Gly Arg Trp Asn Asp Val Cys Gln Arg Pro Tyr
225                 230                 235                 240

His Trp Val Cys Glu Ala Gly Leu Gly Gln Thr Ser Gln Glu Ser His
                245                 250                 255

Gly Gly Gly Gly Ser Asp Ile Lys Leu Gln Gln Ser Gly Ala Glu Leu
                260                 265                 270

Ala Arg Pro Gly Ala Ser Val Lys Met Ser Cys Lys Thr Ser Gly Tyr
            275                 280                 285

Thr Phe Thr Arg Tyr Thr Met His Trp Val Lys Gln Arg Pro Gly Gln
        290                 295                 300

Gly Leu Glu Trp Ile Gly Tyr Ile Asn Pro Ser Arg Gly Tyr Thr Asn
305                 310                 315                 320

Tyr Asn Gln Lys Phe Lys Asp Lys Ala Thr Leu Thr Thr Asp Lys Ser
                325                 330                 335

Ser Ser Thr Ala Tyr Met Gln Leu Ser Ser Leu Thr Ser Glu Asp Ser
                340                 345                 350

Ala Val Tyr Tyr Cys Ala Arg Tyr Tyr Asp Asp His Tyr Cys Leu Asp
            355                 360                 365

Tyr Trp Gly Gln Gly Thr Thr Leu Thr Val Ser Ser Val Glu Gly Gly
        370                 375                 380

Ser Gly Gly Ser Gly Gly Ser Gly Gly Ser Gly Gly Val Asp Asp Ile
385                 390                 395                 400

Gln Leu Thr Gln Ser Pro Ala Ile Met Ser Ala Ser Pro Gly Glu Lys
                405                 410                 415

Val Thr Met Thr Cys Arg Ala Ser Ser Ser Val Ser Tyr Met Asn Trp
                420                 425                 430

Tyr Gln Gln Lys Ser Gly Thr Ser Pro Lys Arg Trp Ile Tyr Asp Thr
            435                 440                 445

Ser Lys Val Ala Ser Gly Val Pro Tyr Arg Phe Ser Gly Ser Gly Ser
        450                 455                 460

Gly Thr Ser Tyr Ser Leu Thr Ile Ser Ser Met Glu Ala Glu Asp Ala
465                 470                 475                 480

Ala Thr Tyr Tyr Cys Gln Gln Trp Ser Ser Asn Pro Leu Thr Phe Gly
                485                 490                 495

Ala Gly Thr Lys Leu Glu Leu Lys His His His His His
            500                 505                 510

<210> SEQ ID NO 18
<211> LENGTH: 1604
<212> TYPE: DNA
<213> ORGANISM: Artificial Sequence
<220> FEATURE:
<223> OTHER INFORMATION: Chemically Synthesized

<400> SEQUENCE: 18
gaattcccgc cgccaccatg ggttggtctt gcatcatcct gttcctggtc gccactgcta      60
ctggggtcca ctcttctaac gacatctact ttaactttca gcgtttcaat gagacaaacc     120
tgatcctgca gagggacgcc agcgtgtcca gctctggcca gctgcggctg accaacctga     180
atggcaacgg agagccaagg gtgggctccc tgggacgggc cttctattcc gccccatcc      240
```

-continued

```
agatctggga caataccaca ggcacagtgg cctccttcgc cacctccttc accttcaaca    300
tccaagtgcc caacaatgcc ggccctgctg atggcctggc cttcgctctg gtgccagtgg    360
gctctcagcc caaggacaag ggcggcttcc tgggcctctt tgatggcagc aattctaact    420
tccacaccgt ggctgtggag tttgacacac tgtacaataa ggactgggac cccaccgaga    480
ggcatatcgg catcgacgtg aactccatca gaagcatcaa gaccacaaga tgggattttg    540
tgaatggcga gaacgccgag gtcctgatca cctatgattc cagcacaaac ctgctggtgg    600
ctagcctggt gtaccctct cagaagacct ccttcatcgt gagcgataca gtggatctga    660
agtctgtgct gcctgagtgg gtgtctgtgg gcttttccgc caccaccggc atcaataagg    720
gcaacgtgga gaccaatgac gtgctgtcct ggagctttgc ctctaagctg tccgatggca    780
ccacatctga gggcctgaat ctggctaacc tggtgctgaa caagatcctg ggcggcggcg    840
gctctgacat caagctgcag cagtccggag ctgagctggc taggcctgga gctagcgtga    900
agatgtcttg caagacctcc ggctacacct tcacaaggta tacaatgcac tgggtcaagc    960
agagacccgg ccagggcctg gagtggatcg gctatatcaa tccttcccgg ggctatacca   1020
attataacca gaagtttaag gacaaggcca ccctgaccac cgataagtct tccagcacag   1080
cttatatgca gctgtcttcc ctgaccagcg aggactctgc cgtgtactat tgcgctaggt   1140
actatgacga tcattactgt ctggattatt ggggccaagg caccacactg acagtgagct   1200
ctgtggaggg aggctccgga ggcagcggag gctctggagg ctccggagga gtggacgaca   1260
tccagctgac ccagtcccct gccatcatgt ctgcttcccc cggcgagaag gtcaccatga   1320
catgcagggc ctccagctct gtgagctaca tgaactggta tcagcagaag agcggcacat   1380
ctcctaagag atggatctac gacaccagca aggtggcctc tggcgtgcca tataggttca   1440
gcggctctgg ctccggcacc agctactctc tgacaatctc cagcatggag gctgaggatg   1500
ccgctaccta ctattgtcag cagtggtctt ccaatcctct gacatttggg gctgggacta   1560
aactggaact gaaacaccac caccaccacc actgataatc taga                    1604
```

GLYCAN-DEPENDENT IMMUNOTHERAPEUTIC MOLECULES

CROSS-REFERENCES TO RELATED APPLICATIONS

This application is a U.S. national phase application filed under 35 U.S.C. § 371 claiming benefit to International Patent Application No. PCT/US2016/030113, filed Apr. 29, 2016, which is entitled to priority under 35 U.S.C. § 119(e) to U.S. Provisional Patent Application No. 62/155,761 filed on May 1, 2015, each of which applications is hereby incorporated herein by reference in its entirety.

BACKGROUND OF THE INVENTION

Alongside the classical approach of chemotherapy and radiotherapy, monoclonal antibodies have been developed as promising drugs to treat cancer. Monoclonal antibodies targeting proteins that are overexpressed on tumor cells can be conjugated with chemotherapeutic drugs or radioisotopes in order to induce death of their binding partners, predominantly the malignant cells. Moreover, naked monoclonal antibodies can utilize the patient's own immune system to mediate killing of their binding partners through the immune mechanism of antibody-dependent cellular cytotoxicity (ADCC). Immune effector cells, such as Natural killer (NK) cells, macrophages and neutrophils, possess Fc receptors that recognize the Fc chain of the therapeutic antibody, thereby leading to target cell destruction. Antibodies recruit these Fc receptor expressing effector cells of the immune system, however these cells only make up a minority of the effector population. This limits their clinical efficacy.

The most powerful and abundant effectors are T cells. However T cells do not have Fc receptors. To utilize the effector function of the T cells, a class of bispecific antibodies has been engineered to have the ability to bind both the T cells and the cancer cells. The concept of using bispecific antibodies to recruit T cells for cancer cell killing was shown in 1985 (Staerz et al. 1985, Nature, 314: 628-631). Since then, different formats/structures of bispecific antibodies have been generated. The latest and the most successful bispecific antibody is the Bispecific T cell engager (BiTE) antibody. In 2014, the FDA approved a BiTE antibody, Blinatumomab (Blincyto) which binds CD3 on T cells and CD19 on B cells, to treat Philadelphia chromosome-negative precursor B-cell acute lymphoblastic leukemia (B-cell ALL), an uncommon form of ALL. The BiTE antibody is a bispecific single chain polypeptide composed of two binding arms connected by a short sequence of peptide. Each arm or single-chain variable fragment (scFv) is derived from the variable heavy and light chains of a monoclonal antibody. For example, Blincyto is derived by connecting the binding domains of anti-human CD3 with anti-human CD19.

There are several issues with utilizing monoclonal or BiTE to target cancer antigens. First, in order to generate a cancer targeting monoclonal antibody, a specific antigen must first be identified on the cancer cell. Indeed, by 2012 the U.S. Food and Drug Administration (FDA) had only approved 12 monoclonal antibodies to treat specific types of cancers (Scott et al., 2012, Nat Rev Cancer, 12: 278-287). In addition, a lack of shared protein antigens across different cancer types greatly limits the number of cancers that may be targeted by a single chimeric BiTE protein. Thus, many unique BiTE proteins will need to be generated for individual cancers, greatly increasing development costs. Finally, tumor specific antigens are frequently also expressed in normal tissue, but at lower levels. Thus, normal tissue may also be targeted for killing. All of these issues can be seen with Blincyto as 1) it targets a single and a rare treatment failure cancer with only ~1000 cases per year in the United States and 2) it targets CD19, which is expressed in normal B cells, leading to normal B cell depletion in addition to cancer cell killing. A better approach would target an antigen present in multiple common cancers that has limited or no expression in normal tissue.

Thus there is a need in the art for improved compositions and methods for treating cancer. The present invention satisfies this unmet need.

SUMMARY OF THE INVENTION

In one aspect, the present invention provides a composition for treating cancer comprising a peptide comprising a tumor-associated carbohydrate antigen (TACA)-binding domain derived from a lectin, wherein the TACA-binding domain specifically binds to a TACA of a tumor cell. In one embodiment, the lectin is selected from the group consisting of a mammalian lectin, human lectin, plant lectin, bacterial lectin, viral lectin, fungal lectin, and protozoan lectin.

In one embodiment, the lectin is selected from the group consisting of a galectin, a siglec, a selectin; a C-type lectin; CD301, L-PHA (*Phaseolus vulgaris* leukoagglutinin); E-PHA (*Phaseolus vulgaris* erythroagglutenin); tomato lectin (*Lycopersicon esculentum* lectin; LEA); peanut lectin (*Arachis hypogaea* Agglutinin; PNA); potato lectin (*Solanum tuberosum* lectin), pokeweed mitogen (*Phytolacca American* lectin), wheat germ agglutinin (*Triticum* Vulgaris lectin); *Artocarpus polyphemus* lectin (Jacalin letin); *Vicia villosa* Agglutinin (VVA); *Helix pomatia* Agglutinin (HPA); *Wisteria floribunda* Agglutinin (WFA); *Sambucus nigra* Agglutinin (SNA), BC2L-CNt (lectin from the gram negative bacteria *Burkholderia cenocepacia*), *Maackia amurensis* leukoagglutinin (MAL), *Psathyrella velutina* (PVL), *Sclerotium rolfsii* lectin (SRL), *Eucheuma serra* agglutinin (ESA), CLEC17A (Prolectin), *Aleuria aurantia* lectin, *Sambucus sieboldiana* lectin (SSA), *Glechoma hederacea* lectin (Gleheda), *Morus nigra* agglutinin (Morniga G), *Salvia sclarea* lectin, *Salvia bogotensis* lectin, *Salvia horminum* lectin, *Clerodendrum trichotomum* lectin, *Moluccella laevis* lectin, *Griffonia simplicifolia* (GsLA4), *Psophocarpus tetragonolobus* (acidic WBAI), *Abrus precatorius* lectin, *Molucella laevis* lectin (MLL), *Amaranthus caudatus* lectin, *Amaranthus leucocarpus* lectin, Laelia *autumnalis* lectin, *Artocarpus integrifolia* lectin, *Maclura pomifera* lectin, *Artocarpus lakoocha* lectin, *Dolichos biflorusagglutinin*, *Dolichos biflorus* lectin, *Glycine max* lectin, and *Agaricus bisporus* lectin.

In one embodiment, the galectin is selected from the group consisting of galectin-1, galectin-2, galectin-3, galectin-4, galectin-5, galectin-6, galectin-7, galectin-8, galectin-9, galectin-10, galectin-11, galectin-12, galectin-13, galectin-14 and galectin-15.

In one embodiment, the siglec is selected from the group consisting of siglec-1 (sialoadhesion), siglec-2 (CD22), siglec-3 (CD33), siglec-4 (myelin associated glycoprotein), siglec-5, siglec-6, siglec-7, siglec-8, siglec-9, siglec-10, siglec-11, siglec-12, siglec-13, siglec-14, siglec-15, siglec-16, siglec-17, Siglec E, Siglec F, siglec G and siglec H.

In one embodiment, the TACA-binding domain binds to a TACA selected from the group consisting of β1, 6 branching, T antigen, sialyl-T epitopes, Tn epitopes, sialyl-Tn epitopes, α2, 6 sialylation, Sialylation, sialyl-Lewis$^{x/a}$, disialyl-Lewis$^{x/a}$, sialyl 6-sulfo Lexis$^x$, Globo H, GD2, GD3, GM3, and Fucosyl GM1. In one embodiment, the TACA-binding domain binds to β1,6GlcNAc-branched N-glycans of a tumor cell. In one embodiment, the TACA-binding domain comprises an amino acid sequence selected from the group consisting of SEQ ID NO: 1, an amino acid sequence having greater than about 90% homology to SEQ ID NO: 1, SEQ ID NO: 2, an amino acid sequence having greater than about 90% homology to SEQ ID NO: 2, SEQ ID NO: 3, an amino acid sequence having greater than about 90% homology to SEQ ID NO: 3, SEQ ID NO: 4, an amino acid sequence having greater than about 90% homology to SEQ ID NO: 4, SEQ ID NO: 5, an amino acid sequence having greater than about 90% homology to SEQ ID NO: 5, SEQ ID NO: 6, an amino acid sequence having greater than about 90% homology to SEQ ID NO: 6, SEQ ID NO: 7, and an amino acid sequence having greater than about 90% homology to SEQ ID NO: 7.

In one embodiment, the peptide is an Fc fusion peptide comprising the TACA-biding domain linked to an Fc domain.

In one embodiment, the peptide further comprises a domain that specifically binds to an immune effector cell. In one embodiment, the immune effector cell is selected from the group consisting of T cells, natural killer (NK) cells, natural killer T (NKT) cells, macrophages, monocytes, dendritic cells, and neutrophils.

In one embodiment, the domain that specifically binds to an immune effector cell comprises a T-cell-binding domain, where the T-cell-binding domain specifically binds to a T-cell. In one embodiment, the T-cell-binding domain binds to at least one of the group consisting of CD3, T-cell receptor, CD2, CD28, and CD25. In one embodiment, the T-cell binding domain comprises an amino acid sequence selected from the group consisting of SEQ ID NO: 9 and an amino acid sequence having greater than about 90% homology to SEQ ID NO: 9. In one embodiment, the peptide comprises an amino acid sequence selected from the group consisting of SEQ ID NO: 11, an amino acid sequence having greater than about 90% homology to SEQ ID NO: 11, SEQ ID NO: 12, an amino acid sequence having greater than about 90% homology to SEQ ID NO: 12, SEQ ID NO: 13, an amino acid sequence having greater than about 90% homology to SEQ ID NO: 13, SEQ ID NO: 14, an amino acid sequence having greater than about 90% homology to SEQ ID NO: 14, SEQ ID NO: 15, an amino acid sequence having greater than about 90% homology to SEQ ID NO: 15, SEQ ID NO: 16, an amino acid sequence having greater than about 90% homology to SEQ ID NO: 16, SEQ ID NO: 17, and an amino acid sequence having greater than about 90% homology to SEQ ID NO: 17.

In one embodiment, the domain that specifically binds to an immune effector cell comprises a NK-cell-binding domain, where the NK-cell-binding domain specifically binds to a NK-cell. In one embodiment, the NK-cell-binding domain binds to at least one of the group consisting of CD16 and NKG2D.

In one embodiment, the peptide comprises a chimeric antigen receptor (CAR) comprising the TACA-binding domain.

In one aspect, the present invention provides a composition for treating cancer comprising an isolated nucleic acid molecule encoding a peptide comprising a tumor-associated carbohydrate antigen (TACA)-binding domain derived from a lectin, wherein the TACA-binding domain specifically binds to a TACA of a tumor cell. In one embodiment, the lectin is selected from the group consisting of a mammalian lectin, human lectin, plant lectin, bacterial lectin, viral lectin, fungal lectin, and protozoan lectin.

In one embodiment, the lectin is selected from the group consisting of a galectin, a siglec, a selectin; a C-type lectin; CD301, L-PHA (*Phaseolus vulgaris* leukoagglutinin); E-PHA (*Phaseolus vulgaris* erythroagglutinen); tomato lectin (*Lycopersicon esculentum* lectin; LEA); peanut lectin (*Arachis hypogaea* Agglutinin; PNA); potato lectin (*Solanum tuberosum* lectin), pokeweed mitogen (*Phytolacca American* lectin), wheat germ agglutinin (*Triticum Vulgaris* lectin); *Artocarpus polyphemus* lectin (Jacalin letin); *Vicia villosa* Agglutinin (VVA); *Helix pomatia* Agglutinin (HPA); *Wisteria floribunda* Agglutinin (WFA); *Sambucus nigra* Agglutinin (SNA), BC2L-CNt (lectin from the gram negative bacteria *Burkholderia cenocepacia*), *Maackia amurensis* leukoagglutinin (MAL), *Psathyrella velutina* (PVL), *Sclerotium rolfsii* lectin (SRL), *Eucheuma serra* agglutinin (ESA), CLEC17A (Prolectin), *Aleuria aurantia* lectin, *Sambucus sieboldiana* lectin (SSA), *Glechoma hederacea* lectin (Gleheda), *Morus nigra* agglutinin (Morniga G), *Salvia sclarea* lectin, *Salvia bogotensis* lectin, *Salvia horminum* lectin, *Clerodendrum trichotomum* lectin, *Moluccella laevis* lectin, *Griffonia simplicifolia* (GsLA4), *Psophocarpus tetragonolobus* (acidic WBAI), *Abrus precatorius* lectin, *Molucella laevis* lectin (MLL), *Amaranthus caudatus* lectin, *Amaranthus leucocarpus* lectin, Laelia *autumnalis* lectin, *Artocarpus integrifolia* lectin, *Maclura pomifera* lectin, *Artocarpus lakoocha* lectin, *Dolichos* biflorusagglutinin, *Dolichos biflorus* lectin, *Glycine max* lectin, and *Agaricus bisporus* lectin.

In one embodiment, the galectin is selected from the group consisting of galectin-1, galectin-2, galectin-3, galectin-4, galectin-5, galectin-6, galectin-7, galectin-8, galectin-9, galectin-10, galectin-11, galectin-12, galectin-13, galectin-14 and galectin-15.

In one embodiment, the siglec is selected from the group consisting of siglec-1 (sialoadhesion), siglec-2 (CD22), siglec-3 (CD33), siglec-4 (myelin associated glycoprotein), siglec-5, siglec-6, siglec-7, siglec-8, siglec-9, siglec-10, siglec-11, siglec-12, siglec-13, siglec-14, siglec-15, siglec-16, siglec-17, Siglec E, Siglec F, siglec G and siglec H.

In one embodiment, the TACA-binding domain binds to a TACA selected from the group consisting of β1, 6 branching, T antigen, sialyl-T epitopes, Tn epitopes, sialyl-Tn epitopes, α2, 6 sialylation, Sialylation, sialyl-Lewis$^{x/a}$, di-sialyl-Lewis$^{x/a}$, sialyl 6-sulfo Lexis$^x$, Globo H, GD2, GD3, GM3, and Fucosyl GM1. In one embodiment, the TACA-binding domain binds to β1,6GlcNAc-branched N-glycans of a tumor cell. In one embodiment, the nucleic acid molecule comprises a nucleotide sequence encoding a TACA-binding domain comprising an amino acid sequence selected from the group consisting of SEQ ID NO: 1, an amino acid sequence having greater than about 90% homology to SEQ ID NO: 1, SEQ ID NO: 2, an amino acid sequence having greater than about 90% homology to SEQ ID NO: 2, SEQ ID NO: 3, an amino acid sequence having greater than about 90% homology to SEQ ID NO: 3, SEQ ID NO: 4, an amino acid sequence having greater than about 90% homology to SEQ ID NO: 4, SEQ ID NO: 5, an amino acid sequence having greater than about 90% homology to SEQ ID NO: 5, SEQ ID NO: 6, an amino acid sequence having greater than about 90% homology to SEQ ID NO: 6, SEQ ID NO: 7, and an amino acid sequence having greater than about 90% homology to SEQ ID NO: 7.

In one embodiment, the peptide encoded by the nucleic acid molecule is an Fc fusion peptide comprising the TACA-biding domain linked to an Fc domain.

In one embodiment, the peptide encoded by the nucleic acid molecule further comprises a domain that specifically binds to an immune effector cell. In one embodiment, the immune effector cell is selected from the group consisting of T cells, natural killer (NK) cells, natural killer T (NKT) cells, macrophages, monocytes, dendritic cells, and neutrophils.

In one embodiment, the domain that specifically binds to an immune effector cell comprises a T-cell-binding domain, where the T-cell-binding domain specifically binds to a T-cell. In one embodiment, the T-cell-binding domain binds to at least one of the group consisting of CD3, T-cell receptor, CD2, CD28, and CD25. In one embodiment, the nucleic acid molecule comprises a nucleotide sequence encoding a T-cell binding domain comprising an amino acid sequence selected from the group consisting of SEQ ID NO: 9 and an amino acid sequence having greater than about 90% homology to SEQ ID NO: 9. In one embodiment, the nucleic acid molecule comprises a nucleotide sequence encoding a peptide comprising an amino acid sequence selected from the group consisting of SEQ ID NO: 11, an amino acid sequence having greater than about 90% homology to SEQ ID NO: 11, SEQ ID NO: 12, an amino acid sequence having greater than about 90% homology to SEQ ID NO: 12, SEQ ID NO: 13, an amino acid sequence having greater than about 90% homology to SEQ ID NO: 13, SEQ ID NO: 14, an amino acid sequence having greater than about 90% homology to SEQ ID NO: 14, SEQ ID NO: 15, an amino acid sequence having greater than about 90% homology to SEQ ID NO: 15, SEQ ID NO: 16, an amino acid sequence having greater than about 90% homology to SEQ ID NO: 16, SEQ ID NO: 17, and an amino acid sequence having greater than about 90% homology to SEQ ID NO: 17.

In one embodiment, the domain that specifically binds to an immune effector cell comprises a NK-cell-binding domain, where the NK-cell-binding domain specifically binds to a NK-cell. In one embodiment, the NK-cell-binding domain binds to at least one of the group consisting of CD16 and NKG2D.

In one embodiment, the nucleic acid molecule encodes a chimeric antigen receptor (CAR) comprising an antigen recognition domain and an intracellular domain, wherein the antigen recognition domain comprises the TACA-binding domain. In one embodiment, the antigen recognition domain of the CAR encoded by the nucleic acid molecule comprises a TACA-binding domain comprising an amino acid sequence selected from the group consisting of SEQ ID NO: 1, an amino acid sequence having greater than about 90% homology to SEQ ID NO: 1, SEQ ID NO: 2, an amino acid sequence having greater than about 90% homology to SEQ ID NO: 2, SEQ ID NO: 3, an amino acid sequence having greater than about 90% homology to SEQ ID NO: 3, SEQ ID NO: 4, an amino acid sequence having greater than about 90% homology to SEQ ID NO: 4, SEQ ID NO: 5, an amino acid sequence having greater than about 90% homology to SEQ ID NO: 5, SEQ ID NO: 6, an amino acid sequence having greater than about 90% homology to SEQ ID NO: 6, SEQ ID NO: 7, and an amino acid sequence having greater than about 90% homology to SEQ ID NO: 7. In one embodiment, the intracellular domain of the CAR encoded by the nucleic acid molecule comprises a CD3 zeta signaling domain and a costimulatory domain.

In one embodiment, the isolated nucleic acid molecule comprises an expression vector. In one embodiment, the isolated nucleic acid molecule comprises in vitro transcribed RNA.

In one aspect, the present invention provides a composition for treating cancer comprising an agent that binds to peptide comprising a tumor-associated carbohydrate antigen (TACA)-binding domain derived from a lectin, wherein the TACA-binding domain specifically binds to a TACA of a tumor cell. In one embodiment, the agent comprises lectin-binding domain.

In one aspect, the present invention provides a composition comprising an isolated nucleic acid molecule encoding a peptide that binds to peptide comprising a tumor-associated carbohydrate antigen (TACA)-binding domain derived from a lectin, wherein the TACA-binding domain specifically binds to a TACA of a tumor cell. In one embodiment, the peptide encoded by the nucleic acid molecule comprises a lectin-binding domain. In one embodiment, the isolated nucleic acid molecule encodes a CAR comprising an antigen binding domain and an intracellular domain, wherein the antigen binding domain comprises the lectin-binding domain.

In one aspect, the present invention provides a cell modified to express a peptide comprising a tumor-associated carbohydrate antigen (TACA)-binding domain derived from a lectin, wherein the TACA-binding domain specifically binds to a TACA of a tumor cell. In one aspect, the cell is modified to express a CAR comprising an antigen recognition domain and an intracellular domain, wherein the antigen recognition domain comprises the TACA-binding domain. In one aspect, the cell is selected from the group consisting of a T cell, a Natural Killer (NK) cell, a cytotoxic T lymphocyte (CTL), and a regulatory T cell.

In one aspect, the present invention provides a method of treating cancer in a subject in need thereof, comprising administering to the subject a composition comprising a peptide comprising a tumor-associated carbohydrate antigen (TACA)-binding domain derived from a lectin, wherein the TACA-binding domain specifically binds to a TACA of a tumor cell. In one embodiment, the lectin is selected from the group consisting of a mammalian lectin, human lectin, plant lectin, bacterial lectin, viral lectin, fungal lectin, and protozoan lectin.

In one embodiment, the lectin is selected from the group consisting of a galectin, a siglec, a selectin; a C-type lectin; CD301, L-PHA (*Phaseolus vulgaris* leukoagglutinin); E-PHA (*Phaseolus vulgaris* erythroagglutinen); tomato lectin (*Lycopersicon esculentum* lectin; LEA); peanut lectin (*Arachis hypogaea* Agglutinin; PNA); potato lectin (*Solanum tuberosum* lectin), pokeweed mitogen (*Phytolacca American* lectin), wheat germ agglutinin (*Triticum* Vulgaris lectin); *Artocarpus polyphemus* lectin (Jacalin letin); *Vicia villosa* Agglutinin (VVA); *Helix pomatia* Agglutinin (HPA); *Wisteria floribunda* Agglutinin (WFA); *Sambucus nigra* Agglutinin (SNA), BC2L-CNt (lectin from the gram negative bacteria *Burkholderia cenocepacia*), *Maackia amurensis* leukoagglutinin (MAL), *Psathyrella velutina* (PVL), *Sclerotium rolfsii* lectin (SRL), *Eucheuma serra* agglutinin (ESA), CLECI7A (Prolectin), *Aleuria aurantia* lectin, *Sambucus sieboldiana* lectin (SSA), *Glechoma hederacea* lectin (Gleheda), *Morus nigra* agglutinin (Morniga G), *Salvia sclarea* lectin, *Salvia bogotensis* lectin, *Salvia horminum* lectin, *Clerodendrum trichotomum* lectin, *Moluccella laevis* lectin, *Griffonia simplicifolia* (GsLA4), *Psophocarpus tetragonolobus* (acidic WBAI), *Abrus precatorius* lectin, *Molucella laevis* lectin (MLL), *Amaranthus caudatus* lectin, *Amaranthus* leucocarpus lectin, Laelia *autumnalis* lectin, *Artocarpus integrifolia* lectin, *Maclura pomifera* lectin,

*Artocarpus* lakoocha lectin, *Dolichos* biflorusagglutinin, *Dolichos biflorus* lectin, *Glycine max* lectin, and *Agaricus bisporus* lectin.

In one embodiment, the galectin is selected from the group consisting of galectin-1, galectin-2, galectin-3, galectin-4, galectin-5, galectin-6, galectin-7, galectin-8, galectin-9, galectin-10, galectin-11, galectin-12, galectin-13, galectin-14 and galectin-15.

In one embodiment, the siglec is selected from the group consisting of siglec-1 (sialoadhesion), siglec-2 (CD22), siglec-3 (CD33), siglec-4 (myelin associated glycoprotein), siglec-5, siglec-6, siglec-7, siglec-8, siglec-9, siglec-10, siglec-11, siglec-12, siglec-13, siglec-14, siglec-15, siglec-16, siglec-17, Siglec E, Siglec F, siglec G and siglec H.

In one embodiment, the TACA-binding domain binds to a TACA selected from the group consisting of β1, 6 branching, T antigen, sialyl-T epitopes, Tn epitopes, sialyl-Tn epitopes, α2, 6 sialylation, Sialylation, sialyl-Lewis$^{x/a}$, di-sialyl-Lewis$^{x/a}$, sialyl 6-sulfo Lexis$^x$, Globo H, GD2, GD3, GM3, and Fucosyl GM1. In one embodiment, the TACA-binding domain binds to β1,6GcNAc-branched N-glycans of a tumor cell. In one embodiment, the TACA-binding domain comprises an amino acid sequence selected from the group consisting of SEQ ID NO: 1, an amino acid sequence having greater than about 90% homology to SEQ ID NO: 1, SEQ ID NO: 2, an amino acid sequence having greater than about 90% homology to SEQ ID NO: 2, SEQ ID NO: 3, an amino acid sequence having greater than about 90% homology to SEQ ID NO: 3, SEQ ID NO: 4, an amino acid sequence having greater than about 90% homology to SEQ ID NO: 4, SEQ ID NO: 5, an amino acid sequence having greater than about 90% homology to SEQ ID NO: 5, SEQ ID NO: 6, an amino acid sequence having greater than about 90% homology to SEQ ID NO: 6, SEQ ID NO: 7, and an amino acid sequence having greater than about 90% homology to SEQ ID NO: 7.

In one embodiment, the peptide is an Fc fusion peptide comprising the TACA-biding domain linked to an Fc domain.

In one embodiment, the peptide further comprises a domain that specifically binds to an immune effector cell. In one embodiment, the immune effector cell is selected from the group consisting of T cells, natural killer (NK) cells, natural killer T (NKT) cells, macrophages, monocytes, dendritic cells, and neutrophils.

In one embodiment, the domain that specifically binds to an immune effector cell comprises a T-cell-binding domain, where the T-cell-binding domain specifically binds to a T-cell. In one embodiment, the T-cell-binding domain binds to at least one of the group consisting of CD3, T-cell receptor, CD2, CD28, and CD25. In one embodiment, the T-cell binding domain comprises an amino acid sequence selected from the group consisting of SEQ ID NO: 9 and an amino acid sequence having greater than about 90% homology to SEQ ID NO: 9. In one embodiment, the peptide comprises an amino acid sequence selected from the group consisting of SEQ ID NO: 11, an amino acid sequence having greater than about 90% homology to SEQ ID NO: 11, SEQ ID NO: 12, an amino acid sequence having greater than about 90% homology to SEQ ID NO: 12, SEQ ID NO: 13, an amino acid sequence having greater than about 90% homology to SEQ ID NO: 13, SEQ ID NO: 14, an amino acid sequence having greater than about 90% homology to SEQ ID NO: 14, SEQ ID NO: 15, an amino acid sequence having greater than about 90% homology to SEQ ID NO: 15, SEQ ID NO: 16, an amino acid sequence having greater than about 90% homology to SEQ ID NO: 16, SEQ ID NO: 17, and an amino acid sequence having greater than about 90% homology to SEQ ID NO: 17.

In one embodiment, the domain that specifically binds to an immune effector cell comprises a NK-cell-binding domain, where the NK-cell-binding domain specifically binds to a NK-cell. In one embodiment, the NK-cell-binding domain binds to at least one of the group consisting of CD16 and NKG2D.

In one embodiment, the peptide comprises a chimeric antigen receptor (CAR) comprising the TACA-binding domain.

In one embodiment, subject has a solid tumor which expresses a TACA.

In one aspect, the present invention provides a method for treating cancer in a subject in need thereof, comprising administering to the subject a composition comprising an isolated nucleic acid molecule encoding a peptide comprising a tumor-associated carbohydrate antigen (TACA)-binding domain derived from a lectin, wherein the TACA-binding domain specifically binds to a TACA of a tumor cell. In one embodiment, the lectin is selected from the group consisting of a mammalian lectin, human lectin, plant lectin, bacterial lectin, viral lectin, fungal lectin, and protozoan lectin.

In one embodiment, the lectin is selected from the group consisting of a galectin, a siglec, a selectin; a C-type lectin; CD301, L-PHA (*Phaseolus vulgaris* leukoagglutinin); E-PHA (*Phaseolus vulgaris* erythroagglutinen); tomato lectin (*Lycopersicon esculentum* lectin; LEA); peanut lectin (*Arachis hypogaea* Agglutinin; PNA); potato lectin (*Solanum tuberosum* lectin), pokeweed mitogen (*Phytolacca American* lectin), wheat germ agglutinin (*Triticum* Vulgaris lectin); *Artocarpus polyphemus* lectin (Jacalin letin); *Vicia villosa* Agglutinin (VVA); *Helix pomatia* Agglutinin (HPA); *Wisteria floribunda* Agglutinin (WFA); *Sambucus nigra* Agglutinin (SNA), BC2L-CNt (lectin from the gram negative bacteria *Burkholderia cenocepacia*), *Maackia amurensis* leukoagglutinin (MAL), *Psathyrella velutina* (PVL), *Sclerotium rolfsii* lectin (SRL), *Eucheuma serra* agglutinin (ESA), CLEC17A (Prolectin), *Aleuria aurantia* lectin, *Sambucus sieboldiana* lectin (SSA), *Glechoma hederacea* lectin (Gleheda), *Morus nigra* agglutinin (Morniga G), *Salvia sclarea* lectin, *Salvia* bogotensis lectin, *Salvia* horminum lectin, *Clerodendrum trichotomum* lectin, *Moluccella laevis* lectin, *Griffonia simplicifolia* (GsLA4), *Psophocarpus tetragonolobus* (acidic WBAI), *Abrus precatorius* lectin, *Molucella laevis* lectin (MLL), *Amaranthus caudatus* lectin, *Amaranthus leucocarpus* lectin, Laelia *autumnalis* lectin, *Artocarpus integrifolia* lectin, *Maclura pomifera* lectin, *Artocarpus* lakoocha lectin, *Dolichos* biflorusagglutinin, *Dolichos biflorus* lectin, *Glycine max* lectin, and *Agaricus bisporus* lectin.

In one embodiment, the galectin is selected from the group consisting of galectin-1, galectin-2, galectin-3, galectin-4, galectin-5, galectin-6, galectin-7, galectin-8, galectin-9, galectin-10, galectin-11, galectin-12, galectin-13, galectin-14 and galectin-15.

In one embodiment, the siglec is selected from the group consisting of siglec-1 (sialoadhesion), siglec-2 (CD22), siglec-3 (CD33), siglec-4 (myelin associated glycoprotein), siglec-5, siglec-6, siglec-7, siglec-8, siglec-9, siglec-10, siglec-11, siglec-12, siglec-13, siglec-14, siglec-15, siglec-16, siglec-17, Siglec E, Siglec F, siglec G and siglec H.

In one embodiment, the TACA-binding domain binds to a TACA selected from the group consisting of β1, 6 branching, T antigen, sialyl-T epitopes, Tn epitopes, sialyl-Tn epitopes, α2, 6 sialylation, Sialylation, sialyl-Lewis$^{x/a}$, disialyl-Lewis$^{x/a}$, sialyl 6-sulfo Lexis$^x$, Globo H, GD2, GD3, GM3, and Fucosyl GM1. In one embodiment, the TACA-binding domain binds to β1,6GlcNAc-branched N-glycans of a tumor cell. In one embodiment, the nucleic acid molecule comprises a nucleotide sequence encoding a TACA-binding domain comprising an amino acid sequence selected from the group consisting of SEQ ID NO: 1, an amino acid sequence having greater than about 90% homology to SEQ ID NO: 1, SEQ ID NO: 2, an amino acid sequence having greater than about 90% homology to SEQ ID NO: 2, SEQ ID NO: 3, an amino acid sequence having greater than about 90% homology to SEQ ID NO: 3, SEQ ID NO: 4, an amino acid sequence having greater than about 90% homology to SEQ ID NO: 4, SEQ ID NO: 5, an amino acid sequence having greater than about 90% homology to SEQ ID NO: 5, SEQ ID NO: 6, an amino acid sequence having greater than about 90% homology to SEQ ID NO: 6, SEQ ID NO: 7, and an amino acid sequence having greater than about 90% homology to SEQ ID NO: 7.

In one embodiment, the peptide encoded by the nucleic acid molecule is an Fc fusion peptide comprising the TACA-biding domain linked to an Fc domain.

In one embodiment, the peptide encoded by the nucleic acid molecule further comprises a domain that specifically binds to an immune effector cell. In one embodiment, the immune effector cell is selected from the group consisting of T cells, natural killer (NK) cells, natural killer T (NKT) cells, macrophages, monocytes, dendritic cells, and neutrophils.

In one embodiment, the domain that specifically binds to an immune effector cell comprises a T-cell-binding domain, where the T-cell-binding domain specifically binds to a T-cell. In one embodiment, the T-cell-binding domain binds to at least one of the group consisting of CD3, T-cell receptor, CD2, CD28, and CD25. In one embodiment, the nucleic acid molecule comprises a nucleotide sequence encoding a T-cell binding domain comprising an amino acid sequence selected from the group consisting of SEQ ID NO: 9 and an amino acid sequence having greater than about 90% homology to SEQ ID NO: 9. In one embodiment, the nucleic acid molecule comprises a nucleotide sequence encoding a peptide comprising an amino acid sequence selected from the group consisting of SEQ ID NO: 11, an amino acid sequence having greater than about 90% homology to SEQ ID NO: 11, SEQ ID NO: 12, an amino acid sequence having greater than about 90% homology to SEQ ID NO: 12, SEQ ID NO: 13, an amino acid sequence having greater than about 90% homology to SEQ ID NO: 13, SEQ ID NO: 14, an amino acid sequence having greater than about 90% homology to SEQ ID NO: 14, SEQ ID NO: 15, an amino acid sequence having greater than about 90% homology to SEQ ID NO: 15, SEQ ID NO: 16, an amino acid sequence having greater than about 90% homology to SEQ ID NO: 16, SEQ ID NO: 17, and an amino acid sequence having greater than about 90% homology to SEQ ID NO: 17.

In one embodiment, the domain that specifically binds to an immune effector cell comprises a NK-cell-binding domain, where the NK-cell-binding domain specifically binds to a NK-cell. In one embodiment, the NK-cell-binding domain binds to at least one of the group consisting of CD16 and NKG2D.

In one embodiment, the nucleic acid molecule encodes a chimeric antigen receptor (CAR) comprising an antigen recognition domain and an intracellular domain, wherein the antigen recognition domain comprises the TACA-binding domain. In one embodiment, the antigen recognition domain of the CAR encoded by the nucleic acid molecule comprises a TACA-binding domain comprising an amino acid sequence selected from the group consisting of SEQ ID NO: 1, an amino acid sequence having greater than about 90% homology to SEQ ID NO: 1, SEQ ID NO: 2, an amino acid sequence having greater than about 90% homology to SEQ ID NO: 2, SEQ ID NO: 3, an amino acid sequence having greater than about 90% homology to SEQ ID NO: 3, SEQ ID NO: 4, an amino acid sequence having greater than about 90% homology to SEQ ID NO: 4, SEQ ID NO: 5, an amino acid sequence having greater than about 90% homology to SEQ ID NO: 5, SEQ ID NO: 6, an amino acid sequence having greater than about 90% homology to SEQ ID NO: 6, SEQ ID NO: 7, and an amino acid sequence having greater than about 90% homology to SEQ ID NO: 7. In one embodiment, the intracellular domain of the CAR encoded by the nucleic acid molecule comprises a CD3 zeta signaling domain and a costimulatory domain.

In one embodiment, the isolated nucleic acid molecule comprises an expression vector. In one embodiment, the isolated nucleic acid molecule comprises in vitro transcribed RNA.

In one embodiment, the subject has a solid tumor which expresses a TACA.

In one aspect, the present invention provides a method of treating cancer in a subject in need thereof, comprising administering to the subject a cell modified to express a peptide comprising a tumor-associated carbohydrate antigen (TACA)-binding domain derived from a lectin, wherein the TACA-binding domain specifically binds to a TACA of a tumor cell.

In one embodiment, the cell is modified to express a CAR comprising an antigen recognition domain and an intracellular domain, wherein the antigen recognition domain comprises the TACA-binding domain. In one embodiment, the cell is selected from the group consisting of a T cell, a Natural Killer (NK) cell, a cytotoxic T lymphocyte (CTL), and a regulatory T cell. In one embodiment, the cell is autologous.

In one aspect, the present invention provides a method of treating cancer in a subject in need thereof comprising a.) administering to the subject a first composition comprising an agent that binds to peptide comprising a tumor-associated carbohydrate antigen (TACA)-binding domain derived from a lectin, and b) administering to the subject a second composition comprising the peptide comprising the TACA-binding domain.

In one aspect, the present invention provides a method of treating cancer in a subject in need thereof comprising a.) administering to the subject a cell modified to express a CAR comprising an antigen binding domain that binds to peptide comprising a tumor-associated carbohydrate antigen (TACA)-binding domain derived from a lectin, and b) administering to the subject a composition comprising the peptide comprising the TACA-binding domain. In one embodiment, the antigen binding domain of the CAR comprises a lectin-binding domain, and wherein the lectin-binding domain binds to the peptide comprising the TACA-binding domain.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 4, comprising

DETAILED DESCRIPTION

Figure 1:
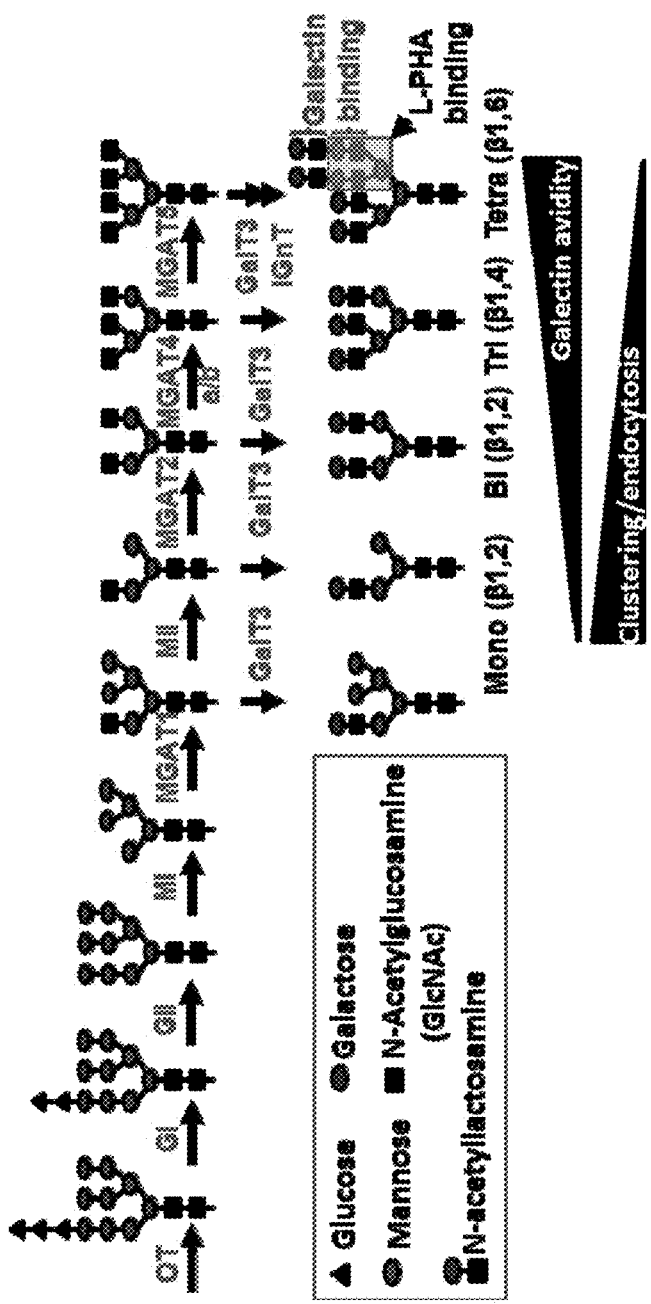
FIG. 1 is an illustration depicting the N-glycosylation branching pathway. Oligosaccharyltransferase transfers a preassembled glycan, $Glc_3Man_9gcNAc_2$ to the NxS/T motifs of glycoproteins in the ER. As glycoproteins transit through the Golgi, the N-acetylglucosaminyltransferase enzymes (Mgat1, Mgat2, Mgat4, and Mgat5) act in a sequential manner to generate branched N-glycans that display increasing affinities for galectins. Galactosyltransferase 3 extends the branches by adding a galactose to GlcNAc creating N-acetyllactosamine which can be bound by galectins. L-PHA binding sites are indicated. GI, glucosidase I; GII, glucosidase II; MI, mannosidase I; MII, mannosidase II; GalT3, Galactosyltransferase 3.

The present invention relates to compositions and methods for treating cancer. In one aspect, the present invention provides a composition comprising a peptide comprising a first domain which specifically binds to a tumor-associated carbohydrate antigen (TACA). In certain embodiments, the peptide comprises a second domain which specifically binds to an immune effector cell. In certain embodiments, the second domain binds to T cell. For example, in certain embodiments, the protein binds to a TACA present on a tumor cell and a biomolecule (e.g., surface protein) present on a T cell, thereby recruiting the T cell to the tumor cell. In certain instances, a peptide, comprising a TACA-binding domain and a T-cell binding domain, is referred to herein as a Glycan-dependent T cell Recruiter (GlyTR). In one embodiment, the composition comprises a chimeric antigen receptor (CAR) comprising a TACA-binding domain. In one embodiment, the composition comprises a nucleic acid molecule encoding the fusion peptide described herein. In one embodiment, the composition comprises a cell genetically modified to express the fusion peptide described herein.

The present invention provides a method of treating cancer in a subject in need thereof. In certain embodiments, the method comprises administering to the subject an effective amount of a composition described herein. For example, in one embodiment, the method comprises administering to the subject a fusion peptide comprising a first domain which binds a TACA and a second domain which binds an immune effector cell, for example a T cell. In one embodiment, the method comprises administering to the subject a composition comprising a nucleic acid molecule encoding a fusion peptide described herein. In one embodiment, the method comprises administering to the subject a composition comprising a cell modified to express a fusion peptide described herein.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

"Activation", as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "lectin" as used herein refers to a protein or peptide that binds carbohydrate structures. A skilled artisan will understand that a lectin is a protein or peptide that is highly specific for binding to sugar moieties.

The term "Tumor Associated Carbohydrate Antigen" or "TACA" as used herein refers to a carbohydrate structure found in cancer. A skilled artisan will understand that a carbohydrate structures consists of one or more linked sugars or monosaccharides. A skilled artisan will understand that carbohydrate structures may be free standing and/or attached to proteins or lipids, known as glycoproteins and glycolipids. A skilled artisan will understand that these carbohydrates structures bind to a lectin.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of the tumor antigen is intended to indicate an abnormal level of expression of the tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types.

"Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention provides compositions and methods for treating cancer as well as other diseases. The cancer may be a hematological malignancy, a solid tumor, a primary or a metastasizing tumor. The compositions of the present invention include peptides comprising a TACA-binding domain, nucleic acid molecules encoding a peptide comprising a TACA-binding domain, a cell modified to express a peptide comprising a TACA-binding domain, and a substrate comprising the peptide, nucleic acid, cell, or combination thereof.

Peptide

In one embodiment, the invention provides a composition comprising a fusion peptide comprising a TACA-binding domain. The TACA-binding domain may comprise any peptide, protein, lectin, lectin fragment, antibody, antibody fragment, small molecule, nucleic acid, or the like, which can specifically bind to a TACA. Exemplary TACAs and their binding partners are listed in Table 1.

Exemplary TACAs include, but is not limited to, β1, 6 branching, T antigen, sialyl-T epitopes, Tn epitopes, sialyl-Tn epitopes, α2, 6 sialylation, Sialylation, sialyl-Lewis$^{x/a}$, di-sialyl-Lewis$^{x/a}$, sialyl 6-sulfo Lexis$^x$, Globo H, GD2, GD3, GM3, and Fucosyl GM1.

In one embodiment, the TACA-binding domain binds to an N-glycan. In certain embodiments, the TACA-binding domain binds to a tri- and tertra-antennary oligosaccharide. In one embodiment, the TACA binding domain binds to β1,6GcNAc-branched N-glycans. In one embodiment, the TACA binding domain binds to Tn epitopes.

TABLE 1

Common TACAs and their binding partners

| TACAs | Carriers | Potential lectin partners |
|---|---|---|
| β1, 6 branching | N-glycans | Galectins, Siglecs, L-PHA, Lycopersicon esculentum lectin (LEA) |
| T antigen | O-linked carbohydrate, Mucins, CD44, β1 integrin, osteopontin | Galectins, Arachis hypogaea Agglutinin (PNA), Artocarpus polyphemus lectin (Jacalin letin) |
| sialyl-T epitopes | O-linked glycans | Galectins, Siglecs |
| Tn epitopes | O-linked glycans | Galectins, Vicia villosa Agglutinin (VVA), Helix pomatia Agglutinin (HPA), Wisteria floribunda Agglutinin (WFA) C-type lectin (i.e., CD301) |
| sialyl-Tn epitopes | O-linked glycans | Siglecs, Galectins, Sambucus nigra Agglutinin (SNA) |
| α2, 6 sialylation | N-glycans | |
| Sialylation | Mucin N-glycans | Selectins, Siglecs, Galectins |
| sialyl-Lewis$^{x/a}$ | Mucins | Selectins |
| di-sialyl-Lewis$^{x/a}$ | Mucins, glycolipids | Selectins |
| sialyl 6-sulfo Lexis$^x$ | | |
| Globo H | Glycolipid | Siglec, galectin, BC2LCM (lectin from the gram negative bacteria Burkholderia cenocepacia) |
| GD2 | Glycolipid | Siglec, galectin |
| GD3 | Glycolipid | Siglec, galectin |
| GM3 | Glycolipid | Siglec, galectin |
| Fucosyl GM1 | Glycolipid | Siglec, galectin |

In certain embodiments, the TACA-binding domain is a peptide sequence derived from a lectin protein. In certain embodiments the lectin is selected from the group consisting of a mammalian lectin, human lectin, plant lectin, bacterial lectin, viral lectin, fungal lectin, and protozoan lectin.

For example, in certain embodiments the TACA-binding domain is derived from a galectin, such as galectin-, galectin-2, galectin-3, galectin-4, galectin-5, galectin-6, galectin-7, galectin-8, galectin-9, galectin-10, galectin-11, galectin-12, galectin-13, galectin-14 and galectin-15; a siglec, such as siglec-1 (sialoadhesion), siglec-2 (CD22), siglec-3 (CD33), siglec-4 (myelin associated glycoprotein), siglec-5, siglec-6, siglec-7, siglec-8, siglec-9, siglec-10, siglec-11, siglec-12, siglec-13, siglec-14, siglec-15, siglec-16, siglec-17, Siglec E, Siglec F, siglec G and siglec H; a selectin; a C-type lectin; CD301, L-PHA (Phaseolus vulgaris leukoagglutinin); E-PHA (Phaseolus vulgaris erythroagglutinen); tomato lectin (Lycopersicon esculentum lectin; LEA); peanut lectin (Arachis hypogaea Agglutinin; PNA); potato lectin (Solanum tuberosum lectin), pokeweed mitogen (Phytolacca American lectin), wheat germ agglutinin (Triticum Vulgaris lectin); Artocarpus polyphemus lectin (Jacalin letin); Vicia villosa Agglutinin (VVA); Helix pomatia Agglutinin (HPA); Wisteria floribunda Agglutinin (WFA); Sambucus nigra Agglutinin (SNA), BC2L-CNt (lectin from the gram negative bacteria Burkholderia cenocepacia) Maackia amurensis leukoagglutinin (MAL), Psathyrella velutina (PVL), Sclerotium rolfsii lectin (SRL), Eucheuma serra agglutinin (ESA), CLEC17A (Prolectin), Aleuria aurantia lectin, Sambucus sieboldiana lectin (SSA), Glechoma hederacea lectin (Gleheda), Morus nigra agglutinin (Morniga G), Salvia sclarea lectin, Salvia bogotensis lectin, Salvia horminum lectin, Clerodendrum trichotomum lectin, Moluccella laevis lectin, Griffonia simplicifolia (GsLA4), Psophocarpus tetragonolobus (acidic WBAI), Abrus precatorius lectin, Molucella laevis lectin (MLL), Amaranthus caudatus lectin, Amaranthus leucocarpus lectin, Laelia autumnalis lectin, Artocarpus integrifolia lectin, Maclura pomifera lectin, Artocarpus lakoocha lectin, Dolichos biflorusagglutinin, Dolichos biflorus lectin, Glycine max lectin, and Agaricus bisporus lectin.

In certain embodiments, the TACA-binding domain is derived from a fragment of a lectin. For example, in one embodiment, the TACA-binding domain comprises a fragment of lectin which retains the ability to bind to the TACA.

In certain embodiments, the TACA-binding domain comprises a mutational variant of a lectin, or fragment thereof. For example, in certain embodiments, the mutational variant displays greater specificity, increased binding affinity, or reduced oligomerization.

In one embodiment, the TACA-binding domain is derived from L-PHA. For example, in one embodiment, the TACA-binding domain comprises the amino acid sequence of SEQ ID NO: 1, depicted below:

```
                                          (SEQ ID NO: 1)
SNDIYFNFQRFNETNLILQRDASVSSSGQLRLTNLNGNGEPRVGSLGRAF

YSAPIQIWDNTTGTVASFATSFTFNIQVPNNAGPADGLAFALVPVGSQPK

DKGGFLGLFDGSNSNFHTVAVEFDTLYNKDWDPTERHIGIDVNSIRSIKT

TRWDFVNGENAEVLITYDSSTNLLVASLVYPSQKTSFIVSDTVDLKSVLP

EWVSVGFSATTGINKGNVETNDVLSWSFASKLSDGTTSEGLNLANLVLNK

IL.
```

In one embodiment, the TACA-binding domain comprises a mutated L-PHA, where L-PHA is truncated at residues 1-5 in order to monomerize the molecule. For example, in one embodiment, the TACA-binding domain comprises the amino acid sequence of SEQ ID NO: 2, depicted below:

(SEQ ID NO: 2)
FNFQRFNETNLILQRDASVSSSGQLRLTNLNGNGEPRVGSLGRAFYSAPI

QIWDNTTGTVASFATSFTFNIQVPNNAGPADGLAFALVPVGSQPKDGGF

LGLFDGSNSNFHTVAVEFDTLYNKDWDPTERHIGIDVNSIRSIKTTRWDF

VNGENAEVLITYDSSTNLLVASLVYPSQKTSFIVSDTVDLKSVLPEWVSV

GFSATTGINKGNVETNDVLSWSFASKLSDGTTSEGLNLANLVLNKIL

In one embodiment, the TACA-binding domain comprises a mutated L-PHA, where L-PHA is mutated to increase binding affinity. For example, in one embodiment, the TACA-binding domain comprises the amino acid sequence of SEQ ID NO: 3, depicted below:

(SEQ ID NO: 3)
ASQTSFSFQRFNETNLILQRDATVSSKGQLRLTNVNDNGEPTLSSLGRAF

YSAPIQIWDNTTGAVAASPTSFTFNIDVPNNSGPADGLAFALVPVGSQPK

DKGGFLGLFDGSNSNFHTVAVEFDTLYNKDWDPKPRHIGIDVNSIKSIKT

TTWDFVKGENAEVLITYDSSTKLLVASLVYPSLKTSFIVSDTVDLKSVLP

EWVIVGFTATTGITKGNVETNDILSWSFASKLSDGTTSEALNLANFALNQ

IL

In one embodiments, the TACA-binding domain comprises a mutated L-PHA, where L-PHA is mutated to monomerize the molecule and increase binding affinity. For example, in one embodiment, the TACA-binding domain comprises the amino acid sequence of SEQ ID NO: 4, depicted below:

(SEQ ID NO: 4)
FSFQRFNETNLILQRDATVSSKGQLRLTNVNDNGEPTLSSLGRAFYSAPI

QIWDNTTGAVAASPTSFTFNIDVPNNSGPADGLAFALVPVGSQPKDGGF

LGLFDGSNSNFHTVAVEFDTLYNKDWDPKPRHIGIDVNSIKSIKTTTWDF

VKGENAEVLITYDSSTKLLVASLVYPSLKTSFIVSDTVDLKSVLPEWVIV

GFTATTGITKGNVETNDILSWSFASKLSDGTTSEALNLANFALNQIL.

In one embodiment, the TACA-binding domain binds to Tn epitope and is derived from VVA (*Vicia villosa* isolectin B). For example, in one embodiment, the TACA-binding domain comprises the amino acid sequence of SEQ ID NO: 5, depicted below:

(SEQ ID NO: 5)
TESTSFSFTNFNPNQNNLILQEDALVNSAGTLELTAVAAGAPVPDSLGRA

LYAAPIHIHDNTTLASFTTSFSFVMAAPAAAAVADGLAFFLAPPDTQPQA

RGGFLGLFADRAHDASYQTVAVEFDTYSNAWDPNYTHIGIDTNGIESKKT

TPFDMVYGEKANIVITYQASTKALAASLVFPVSQTSYAVSARVDLRDILP

EYVRVGFSATTGLNAGVVETHDIVSWSFAVSLA.

In one embodiment, the TACA-binding domain binds to Tn epitope and comprises a mutated VVA (*Vicia villosa* isolectin B), where VVA is truncated at residues 1-5 in order to monomerize the molecule. For example, in one embodiment, the TACA-binding domain comprises the amino acid sequence of SEQ ID NO: 6, depicted below:

(SEQ ID NO: 6)
FSFTNFNPNQNNLILQEDALVNSAGTLELTAVAAGAPVPDSLGRALYAAP

IHIHDNTTLASFTTSFSFVMAAPAAAAVADGLAFFLAPPDTQPQARGGFL

GLFADRAHDASYQTVAVEFDTYSNAWDPNYTHIGIDTNGIESKKTTPFDM

VYGEKANIVITYQASTKALAASLVFPVSQTSYAVSARVDLRDILPEYVRV

GFSATTGLNAGVVETHDIVSWSFAVSLA.

In one embodiment, the TACA-binding domain binds to Tn eptiope and is derived from CD301 (CLEC10A). For example, in one embodiment, the TACA-binding domain comprises the amino acid sequence of SEQ ID NO: 7, depicted below:

(SEQ ID NO: 7)
QNSKFQRDLVTLRTDFSNFTSNTVAEIQALTSQGSSLEETIASLKAEVEG

FKQERQAGVSELQEHTTQKAHLGHCPHCPSVCVPVHSEMLLRVQQLVQDL

KKLTCQVATLNNNASTEGTCCPVNWVEHQDSCYWFSHSGMSWAEAEKYCQ

LKNAHLVVINSREEQNFVQKYLGSAYTWMGLSDPEGAWKWVDGTDYATGF

QNWKPGQPDDWQGHGLGGGEDCAHFHPDGRWNDDVCQRPYHWVCEAGLGQ

TSQESH.

In certain embodiments, the peptide comprises a leader sequence. The leader sequence may function to enhance translation of the peptide, target the peptide to a particular cellular or extracellular location, or direct the secretion of the peptide. In one embodiment, the peptide comprises the leader sequence of the amino acid sequence of SEQ ID NO: 8, depicted below:

(SEQ ID NO: 8)
MGWSCIILFLVATATGVHS.

In certain embodiments, the composition comprises a peptide that binds to a TACA-binding domain described herein. For example, in certain embodiments, the composition comprises a peptide that binds to a lectin-derived TACA-binding peptide. For example, in one embodiment, the composition comprises a lectin-binding domain, where the lectin-binding domain binds to a lectin or lectin-derived peptide which binds to a TACA. For example, the peptide that binds to a TACA-binding domain is an antibody or antibody fragment which specifically binds the TACA-binding domain. In another embodiment, the peptide that binds to a TACA-binding domain may be derived from the associated TACA itself.

In certain embodiments, the composition comprises a fusion protein comprising one or more TACA-binding domains described herein. For example, in one embodiment, the fusion protein comprises one or more TACA-binding domains and one or more targeting domains, where the targeting domains may direct the fusion protein to a particular cell or tissue region. In one embodiment, the fusion protein comprises an Fc fusion protein, comprising one or more TACA-binding domains linked to an antibody Fc domain. In one embodiment, the fusion protein comprises a bispecific antibody comprising one or more TACA-binding domains. In one embodiment, the fusion protein comprises a chimeric antigen receptor (CAR) comprising one or more TACA-binding domains.

In certain embodiments, the composition comprises a fusion protein comprising one or more peptides which bind to a TACA-binding domain described herein. For example, in one embodiment, the composition comprises a fusion protein comprising one or more lectin-binding domains, wherein the lectin-binding domains bind to a lectin or lectin-derived peptide which binds to a TACA. For example, in one embodiment, the fusion protein comprises one or more lectin-binding domains and one or more targeting domains, where the targeting domains may direct the fusion protein to a particular cell or tissue region. In one embodiment, the fusion protein comprises an Fc fusion protein, comprising one or more lectin-binding domains linked to an antibody Fc domain. In one embodiment, the fusion protein comprises a bispecific antibody comprising one or more lectin-binding domains. In one embodiment, the fusion protein comprises a chimeric antigen receptor (CAR) comprising one or more lectin-binding domains.

In one aspect, the composition comprises a peptide having two different binding specificities and thus binds to two different antigens. In one embodiment, the peptide comprises a first antigen recognition domain that binds to a first antigen and a second antigen recognition domain that binds to a second antigen. In one embodiment, the first antigen recognition domain is a TACA-binding domain. Examples of TACAs are described elsewhere herein, all of which may be targeted by the peptide of the present invention.

In certain embodiments, the second antigen recognition domain binds to an immune effector cell. Exemplary immune effector cells include, but is not limited to, T cells, natural killer (NK) cells, natural killer T (NKT) cells, macrophages, monocytes, dendritic cells, and neutrophils.

In one embodiment, the second antigen recognition binds to a NK cell antigen, and is referred to herein as a NK-cell-binding domain.

In one embodiment, the second antigen recognition domain binds to a T cell antigen, as is referred to herein as a T-cell-binding domain.

In certain embodiments, the peptide comprises a bispecific peptide having a TACA-binding domain and an immune effector cell-binding domain. In one embodiment, the peptide comprises a bispecific peptide having a TACA-binding domain and a NK-cell-binding domain. In one embodiment, the peptide comprises a bispecific peptide having a TACA-binding domain and a T cell-binding domain. In one embodiment, the bispecific peptide comprises a human antibody, a humanized antibody, or fragments thereof. In certain embodiments, the bispecific peptide comprises a lectin, lectin fragment, or mutant thereof.

In certain embodiments, the peptide comprises an immune effector cell-binding domain. For example, in one embodiment, the immune effector cell-binding domain comprises a peptide, protein, antibody, or antibody fragment which binds to a biomolecule present on an immune effector cell.

In certain embodiments, the peptide comprises a NK cell-binding domain. For example, in one embodiment, the NK cell binding domain comprises a peptide, protein, antibody, or antibody fragment which binds to a biomolecule present on a NK cell. Exemplary molecules of NK cells to which the NK cell-binding domain may bind include, but not limited to CD16 and NKG2D.

In certain embodiments, the peptide comprises a T cell-binding domain. For example, in one embodiment, the T cell binding domain comprises a peptide, protein, antibody, or antibody fragment which binds to a biomolecule present on a T cell. Exemplary molecules of T-cells to which T-cell-binding domain may bind include, but not limited to CD3, T-cell receptor, CD2, CD28, and CD25. In one embodiment, the T cell binding domain comprises a peptide, protein, antibody, or antibody fragment which binds to CD3 on a T cell.

In one embodiment, the T cell-binding domain comprises an antibody fragment that specifically binds to CD3. For example, in one embodiment, the T-cell binding domain comprises the amino acid sequence of SEQ ID NO: 9 depicted below:

(SEQ ID NO: 9)
DIKLQQSGAELARPGASVKMSCKTSGYTFTRYTMHWVKQRPGQGLEWIGY

INPSRGYTNYNQKFKDKATLTTDKSSSTAYMQLSSLTSEDSAVYYCARYY

DDHYCLDYWGQGTTLTVSSVEGGSGGSGGSGGSGGVDDIQLTQSPAIMSA

SPGEKVTMTCRASSSVSYMNWYQQKSGTSPKRWIYDTSKVASGVPYRFSG

SGSGTSYSLTISSMEAEDAATYYCQQWSSNPLTFGAGTKLELK.

In one embodiment, the peptide, comprises a TACA-binding domain and a T-cell-binding domain. In certain instances, the peptide, comprising a TACA-binding domain and a T-cell binding domain, is referred to as a glycan-dependent T-cell recruiter (GlyTR).

In certain embodiments, the peptide comprises a linker domain between the TACA-binding domain and the immune effector cell binding domain. The linker domain may be of any suitable size or sequence. For example, in one embodiment, the linker domain comprises the amino acid sequence of GGGGS (SEQ ID NO: 10).

In one embodiment, the peptide comprises an amino acid sequence of SEQ ID NO: 11, SEQ ID NO: 12, SEQ ID NO: 13, SEQ ID NO: 14, SEQ ID NO: 15, SEQ ID NO: 16, or SEQ ID NO: 17 (depicted in Example 2). In certain embodiments, the peptide comprises an amino acid sequence of SEQ ID NO: 11, SEQ ID NO: 12, SEQ ID NO: 13, SEQ ID NO: 14, SEQ ID NO: 15, SEQ ID NO: 16, or SEQ ID NO: 17 without the C-terminal His-tag contained therein. Other exemplary peptides include those listed in Table 2. However, the present invention is not limited to any particular TACA-binding domain, immune effector cell-binding domain, NK cell-binding domain, or T-cell-binding domain. Rather any TACA-binding domain, immune effector cell-binding domain, NK cell-binding domain, T-cell binding domain, or combination thereof, may be utilized.

TABLE 2

Examples of GlyTR molecules

| Effector cells | GlyTR formats Effector cell binding arm × TACA binding arm | TACA targets |
| --- | --- | --- |
| T cells | scFv CD3 × L-PHA | β1, 6 branching |
| T cells | scFv CD3 × LEA | β1, 6 branching |
| T cells | scFv CD3 × Galectin 1-15 | β1, 6 branching |
| T cells | scFv CD3 × Siglec 1-17[a] | sialyl-Tn epitopes |
| T cells | scFv CD3 × CD301[a] | Tn epitopes |
| T cells | scFv CD3 × VVAb | Tn epitopes |

[a]Extracellular binding domain

In one embodiment, the peptide of the composition is a chimeric antigen receptor (CAR), comprising a TACA-binding domain described elsewhere herein. In certain embodiments, the CAR further comprises one or more of a hinge domain, transmembrane domain, cytoplasmic domain, costimulatory domain, or zeta chain. CARs, including their transmembrane and cytoplasmic domains, are described in detail for example in U.S. Patent Application Publication Nos: US2013/0287748, US2014/0370017, US2014/0099309, and US2014/0271635, which are incorporated by reference in their entirety. For example, in certain embodiments, the CAR comprises a cytoplasmic domain comprising a costimulatory domain. The costimulatory domain comprises the intracellular domain of a costimulatory molecule. Costimulatory molecules are cell surface molecules other than antigens receptors or their ligands that are required for an efficient response of lymphocytes to antigen.

Preferred examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the invention comprises a cytoplasmic signaling sequence derived from CD3 zeta.

In a preferred embodiment, the cytoplasmic domain of the CAR can be designed to comprise the CD3-zeta signaling domain by itself or combined with any other desired cytoplasmic domain(s) useful in the context of the CAR of the invention. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like.

The peptide of the present invention may be made using chemical methods. For example, peptides can be synthesized by solid phase techniques (Roberge J Y et al (1995) Science 269: 202-204), cleaved from the resin, and purified by preparative high performance liquid chromatography. Automated synthesis may be achieved, for example, using the ABI 431 A Peptide Synthesizer (Perkin Elmer) in accordance with the instructions provided by the manufacturer.

The invention should also be construed to include any form of a peptide having substantial homology to a peptide disclosed herein. Preferably, a peptide which is "substantially homologous" is about 50% homologous, more preferably about 70% homologous, even more preferably about 80% homologous, more preferably about 90% homologous, even more preferably, about 95% homologous, and even more preferably about 99% homologous to amino acid sequence of a peptide disclosed herein.

In certain embodiments, the invention comprises a peptide that is about 50% homologous, about 70% homologous, about 80% homologous, about 90% homologous, about 95% homologous, or about 99% homologous to an amino acid sequence of any of SEQ ID NOs: 1-17.

The peptide may alternatively be made by recombinant means or by cleavage from a longer polypeptide. The composition of a peptide may be confirmed by amino acid analysis or sequencing.

The variants of the peptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the peptide is an alternative splice variant of the peptide of the present invention, (iv) fragments of the peptides and/or (v) one in which the peptide is fused with another peptide, such as a leader or secretory sequence or a sequence which is employed for purification (for example, His-tag) or for detection (for example, Sv5 epitope tag). The fragments include peptides generated via proteolytic cleavage (including multi-site proteolysis) of an original sequence. Variants may be post-translationally, or chemically modified. Such variants are deemed to be within the scope of those skilled in the art from the teaching herein.

As known in the art the "similarity" between two peptides is determined by comparing the amino acid sequence and its conserved amino acid substitutes of one polypeptide to a sequence of a second polypeptide. Variants are defined to include peptide sequences different from the original sequence, preferably different from the original sequence in less than 40% of residues per segment of interest, more preferably different from the original sequence in less than 25% of residues per segment of interest, more preferably different by less than 10% of residues per segment of interest, most preferably different from the original protein sequence in just a few residues per segment of interest and at the same time sufficiently homologous to the original sequence to preserve the functionality of the original sequence and/or the ability to bind to a TACA. The present invention includes amino acid sequences that are at least 60%, 65%, 70%, 72%, 74%, 76%, 78%, 80%, 90%, or 95% similar or identical to the original amino acid sequence. The degree of identity between two peptides is determined using computer algorithms and methods that are widely known for the persons skilled in the art. The identity between two amino acid sequences is preferably determined by using the BLASTP algorithm [BLAST Manual, Altschul, S., et al., NCBI NLM NIH Bethesda, Md. 20894, Altschul, S., et al., J. Mol. Biol. 215: 403-410 (1990)].

The peptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or Xenopus egg extracts (U.S. Pat. No. 6,103,489) to a standard translation reaction.

The peptides of the invention may include unnatural amino acids formed by post-translational modification or by introducing unnatural amino acids during translation. A variety of approaches are available for introducing unnatural amino acids during protein translation.

A peptide or protein of the invention may be conjugated with other molecules, such as proteins, to prepare fusion proteins. This may be accomplished, for example, by the synthesis of N-terminal or C-terminal fusion proteins provided that the resulting fusion protein retains the functionality of the peptide.

A peptide or protein of the invention may be phosphorylated using conventional methods such as the method described in Reedijk et al. (The EMBO Journal 11(4):1365, 1992).

Cyclic derivatives of the peptides of the invention are also part of the present invention. Cyclization may allow the peptide to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position.

It may be desirable to produce a cyclic peptide which is more flexible than the cyclic peptides containing peptide bond linkages as described above. A more flexible peptide may be prepared by introducing cysteines at the right and left position of the peptide and forming a disulphide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

The invention also relates to peptides fused to, or integrated into, a target protein, and/or a targeting domain capable of directing the chimeric protein to a desired cellular component or cell type or tissue. The chimeric proteins may also contain additional amino acid sequences or domains. The chimeric proteins are recombinant in the sense that the various components are from different sources, and as such are not found together in nature (i.e., are heterologous).

In one embodiment, the targeting domain can be a membrane spanning domain, a membrane binding domain, or a sequence directing the protein to associate with for example vesicles or with the nucleus. In one embodiment, the targeting domain can target a peptide to a particular cell type or tissue. For example, the targeting domain can be a cell surface ligand or an antibody against cell surface antigens of a target tissue (e.g., bone, regenerating bone, degenerating bone, cartilage). A targeting domain may target the peptide of the invention to a cellular component.

A peptide of the invention may be synthesized by conventional techniques. For example, the peptides or chimeric proteins may be synthesized by chemical synthesis using solid phase peptide synthesis. These methods employ either solid or solution phase synthesis methods (see for example, J. M. Stewart, and J. D. Young, Solid Phase Peptide Synthesis, $2^{nd}$ Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, suprs, Vol 1, for classical solution synthesis). By way of example, a peptide of the invention may be synthesized using 9-fluorenyl methoxycarbonyl (Fmoc) solid phase chemistry with direct incorporation of phosphothreonine as the N-fluorenylmethoxy-carbonyl-O-benzyl-L-phosphothreonine derivative.

N-terminal or C-terminal fusion proteins comprising a peptide or chimeric protein of the invention conjugated with other molecules may be prepared by fusing, through recombinant techniques, the N-terminal or C-terminal of the peptide or chimeric protein, and the sequence of a selected protein or selectable marker with a desired biological function. The resultant fusion proteins contain the peptide of the invention fused to the selected protein or marker protein as described herein. Examples of proteins which may be used to prepare fusion proteins include immunoglobulins, glutathione-S-transferase (GST), hemagglutinin (HA), and truncated myc.

Peptides of the invention may be developed using a biological expression system. The use of these systems allows the production of large libraries of random peptide sequences and the screening of these libraries for peptide sequences that bind to particular proteins. Libraries may be produced by cloning synthetic DNA that encodes random peptide sequences into appropriate expression vectors (see Christian et al 1992, J. Mol. Biol. 227:711; Devlin et al, 1990 Science 249:404; Cwirla et al 1990, Proc. Natl. Acad, Sci. USA, 87:6378). Libraries may also be constructed by concurrent synthesis of overlapping peptides (see U.S. Pat. No. 4,708,871).

The peptides and chimeric proteins of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

Nucleic Acid

In one embodiment, the present invention provides a composition comprising an isolated nucleic acid encoding a peptide comprising a TACA-binding domain described elsewhere herein.

In one embodiment, the isolated nucleic acid sequence encodes a TACA-binding domain. In certain embodiments, the isolated nucleic acid comprises a sequence encoding a peptide derived from a lectin, including, for example a galectin, such as galectin-1, galectin-2, galectin-3, galectin-4, galectin-5, galectin-6, galectin-7, galectin-8, galectin-9, galectin-10, galectin-11, galectin-12, galectin-13, galectin-14 and galectin-15; a siglec, such as siglec-1 (sialoadhesion), siglec-2 (CD22), siglec-3 (CD33), siglec-4 (myelin associated glycoprotein), siglec-5, siglec-6, siglec-7, siglec-8, siglec-9, siglec-10, siglec-11, siglec-12, siglec-13, siglec-14, siglec-15, siglec-16, siglec-17, Siglec E, Siglec F, siglec G and siglec H; a selectin; a C-type lectin; CD301, L-PHA (*Phaseolus vulgaris* leukoagglutinin); E-PHA (*Phaseolus vulgaris* erythroagglutinen); tomato lectin (*Lycopersicon esculentum* lectin; LEA); peanut lectin (*Arachis hypogaea* Agglutinin; PNA); potato lectin (*Solanum tuberosum* lectin), pokeweed mitogen (*Phytolacca* American lectin), wheat germ agglutinin (*Triticum* Vulgaris lectin) *Artocarpus polyphemus* lectin (Jacalin letin); *Vicia villosa* Agglutinin (VVA); *Helix pomatia* Agglutinin (HPA); *Wisteria floribunda* Agglutinin (WFA); *Sambucus nigra* Agglutinin (SNA), BC2L-CNt (lectin from the gram negative bacteria *Burkholderia cenocepacia*) *Maackia amurensis* leukoagglutinin (MAL), *Psathyrella velutina* (PVL), *Sclerotium rolfsii* lectin (SRL), *Eucheuma serra* agglutinin (ESA), CLEC17A (Prolectin), *Aleuria aurantia* lectin, *Sambucus sieboldiana* lectin (SSA), *Glechoma hederacea* lectin (Gleheda), *Morus nigra* agglutinin (Morniga G), *Salvia sclarea* lectin, *Salvia bogotensis* lectin, *Salvia horminum* lectin, *Clerodendrum trichotomum* lectin, *Moluccella laevis* lectin, *Griffonia simplicifolia* (GsLA4), *Psophocarpus tetragonolobus* (acidic WBAI), *Abrus precatorius* lectin, *Molucella laevis* lectin (MLL), *Amaranthus caudatus* lectin, *Amaranthus* leucocarpus lectin, Laelia *autumnalis* lectin, *Artocarpus integrifolia* lectin, *Maclura pomifera* lectin, *Artocarpus* lakoocha lectin, *Dolichos* biflorusagglutinin, *Dolichos biflorus* lectin, *Glycine max* lectin, and *Agaricus bisporus* lectin.

For example, in various embodiments, the isolated nucleic acid sequence encodes a TACA binding domain comprising an amino acid sequence selected from SEQ ID NO: 1, SEQ ID NO: 2, SEQ ID NO: 3, SEQ ID NO: 4, SEQ ID NO: 5, SEQ ID NO: 6, or SEQ ID NO: 7.

In certain embodiments, the isolated nucleic acid sequence encodes a leader sequence. For example, in certain embodiments, the isolated nucleic acid sequence encodes a leader sequence comprising the amino acid sequence of SEQ ID NO: 8.

In certain embodiments, the isolated nucleic acid sequence encodes a T-cell binding domain. For example, in certain embodiments, the isolated nucleic acid sequence encodes a T-cell-binding domain comprising the amino acid sequence of SEQ ID NO: 9.

In certain embodiments, the isolated nucleic acid sequence encodes a peptide comprising a TACA-binding domain and a T-cell-binding domain. For example, in certain embodiments, the isolated nucleic acid sequence encodes a peptide comprising an amino acid sequence selected from SEQ ID NO: 11, SEQ ID NO: 12, SEQ ID NO: 13, SEQ ID NO: 14, SEQ ID NO: 15, SEQ ID NO: 16, or SEQ ID NO: 17. In certain embodiments, the isolated nucleic acid encodes a peptide comprising an amino acid sequence selected from SEQ ID NO: 11, SEQ ID NO: 12, SEQ ID NO: 13, SEQ ID NO: 14, SEQ ID NO: 15, SEQ ID NO: 16, or SEQ ID NO: 17 without the C-terminal His-tag contained therein.

In one embodiment, the isolated nucleic acid sequence comprises the nucleotide sequence of SEQ ID NO: 18.

In certain embodiments, the isolated nucleic acid sequence encodes a CAR comprising a TACA-binding domain. In certain embodiments, the isolated nucleic acid sequence encodes a CAR comprising a TACA-binding domain and one or more of a transmembrane domain and a cytoplasmic domain.

Further, the invention encompasses an isolated nucleic acid encoding a peptide having substantial homology to a peptide disclosed herein. In certain embodiments, the isolated nucleic acid sequence encodes a peptide having at least 75%, 80%, 85%, 90%, 95%, 96%, 97%, 98%, or 99% sequence homology with an amino acid sequence selected from SEQ ID NOs: 1-17.

Further, the invention encompasses an isolated nucleic acid encoding a peptide having substantial homology to a nucleotide sequence disclosed herein. In certain embodiments, the isolated nucleic acid sequence has at least 75%, 80%, 85%, 90%, 95%, 96%, 97%, 98%, or 99% sequence homology with SEQ ID NO: 18.

The isolated nucleic acid sequence encoding a peptide of the invention can be obtained using any of the many recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The isolated nucleic acid may comprise any type of nucleic acid, including, but not limited to DNA and RNA. For example, in one embodiment, the composition comprises an isolated DNA molecule, including for example, an isolated cDNA molecule, encoding a peptide of the invention, or functional fragment thereof. In one embodiment, the composition comprises an isolated RNA molecule encoding the peptide of the invention, or a functional fragment thereof.

The nucleic acid molecules of the present invention can be modified to improve stability in serum or in growth medium for cell cultures. Modifications can be added to enhance stability, functionality, and/or specificity and to minimize immunostimulatory properties of the nucleic acid molecule of the invention. For example, in order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect function of the molecule.

In one embodiment of the present invention the nucleic acid molecule may contain at least one modified nucleotide analogue. For example, the ends may be stabilized by incorporating modified nucleotide analogues.

Non-limiting examples of nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

Other examples of modifications are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In some instances, the nucleic acid molecule comprises at least one of the following chemical modifications: 2'-H, 2'-O-methyl, or 2'-OH modification of one or more nucleotides. In certain embodiments, a nucleic acid molecule of the invention can have enhanced resistance to nucleases. For increased nuclease resistance, a nucleic acid molecule, can include, for example, 2'-modified ribose units and/or phosphorothioate linkages. For example, the 2' hydroxyl group (OH) can be modified or replaced with a number of different "oxy" or "deoxy" substituents. For increased nuclease resistance the nucleic acid molecules of the invention can include 2'-O-methyl, 2'-fluorine, 2'-O-methoxyethyl, 2'-O-aminopropyl, 2'-amino, and/or phosphorothioate linkages. Inclusion of locked nucleic acids (LNA), ethylene nucleic acids (ENA), e.g., 2'4'-ethylene-bridged nucleic acids, and certain nucleobase modifications such as 2-amino-A, 2-thio (e.g., 2-thio-U), G-clamp modifications, can also increase binding affinity to a target.

In one embodiment, the nucleic acid molecule includes a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In one embodiment, the nucleic acid molecule includes at least one 2'-O-methyl-modified nucleotide, and in some embodiments, all of the nucleotides of the nucleic acid molecule include a 2'-O-methyl modification.

In certain embodiments, the nucleic acid molecule of the invention preferably has one or more of the following properties:

Nucleic acid agents discussed herein include otherwise unmodified RNA and DNA as well as RNA and DNA that have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al. (Nucleic Acids Res., 1994, 22:2183-2196). Such rare or unusual RNAs, often termed modified RNAs, are typically the result of a post-transcriptional modification and are within the term unmodified RNA as used herein. Modified RNA, as used herein, refers to a molecule in which one or more of the components of the nucleic acid, namely sugars, bases, and phosphate moieties, are different from that which occur in nature, preferably different from that which occurs in the human body. While they are referred to as "modified RNAs" they will of course, because of the modification, include molecules that are not, strictly speaking, RNAs. Nucleoside surrogates are molecules in which the ribophosphate backbone is replaced with a non-ribophosphate construct that allows the bases to be presented in the correct spatial relationship such that hybridization is substantially similar to what is seen with a ribophosphate backbone, e.g., non-charged mimics of the ribophosphate backbone.

Modifications of the nucleic acid of the invention may be present at one or more of, a phosphate group, a sugar group, backbone, N-terminus, C-terminus, or nucleobase.

The present invention also includes a vector in which the isolated nucleic acid of the present invention is inserted. The art is replete with suitable vectors that are useful in the present invention.

In brief summary, the expression of natural or synthetic nucleic acids encoding a peptide of the invention is typically achieved by operably linking a nucleic acid encoding the peptide or portions thereof to a promoter, and incorporating the construct into an expression vector. The vectors to be used are suitable for replication and, optionally, integration in eukaryotic cells. Typical vectors contain transcription and translation terminators, initiation sequences, and promoters useful for regulation of the expression of the desired nucleic acid sequence.

The vectors of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The isolated nucleic acid of the invention can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the vector may be provided to a cell in the form of a viral vector. Viral vector technology is well known in the art and is described, for example, in Sambrook et al. (2012, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

For example, vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In one embodiment, the composition includes a vector derived from an adeno-associated virus (AAV). Adeno-associated viral (AAV) vectors have become powerful gene delivery tools for the treatment of various disorders. AAV vectors possess a number of features that render them ideally suited for gene therapy, including a lack of pathogenicity, minimal immunogenicity, and the ability to transduce postmitotic cells in a stable and efficient manner. Expression of a particular gene contained within an AAV vector can be specifically targeted to one or more types of cells by choosing the appropriate combination of AAV serotype, promoter, and delivery method In certain embodiments, the vector also includes conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor −1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Enhancer sequences found on a vector also regulates expression of the gene contained therein. Typically, enhancers are bound with protein factors to enhance the transcription of a gene. Enhancers may be located upstream or downstream of the gene it regulates. Enhancers may also be tissue-specific to enhance transcription in a specific cell or tissue type. In one embodiment, the vector of the present invention comprises one or more enhancers to boost transcription of the gene present within the vector.

In order to assess the expression of a peptide, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

In one embodiment, the isolated nucleic acid encoding a peptide of the invention comprises in vitro transcribed (IVT) RNA. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA.

In one embodiment, the DNA to be used for PCR contains an open reading frame. The DNA can be from a naturally occurring DNA sequence from the genome of an organism. In one embodiment, the DNA is a full length gene of interest of a portion of a gene. The gene can include some or all of the 5' and/or 3' untranslated regions (UTRs). The gene can include exons and introns. In one embodiment, the DNA to be used for PCR is a human gene. In another embodiment, the DNA to be used for PCR is a human gene including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

Genes that can be used as sources of DNA for PCR include genes that encode polypeptides that provide a therapeutic or prophylactic effect to an organism or that can be used to diagnose a disease or disorder in an organism. Preferred genes are genes which are useful for a short term treatment, or where there are safety concerns regarding dosage or the expressed gene. For example, for treatment of cancer, autoimmune disorders, parasitic, viral, bacterial, fungal or other infections, the transgene(s) to be expressed may encode a polypeptide that functions as a ligand or receptor for cells of the immune system, or can function to stimulate or inhibit the immune system of an organism. In some embodiments, it is not desirable to have prolonged ongoing stimulation of the immune system, nor necessary to produce changes which last after successful treatment, since this may then elicit a new problem. For treatment of an autoimmune disorder, it may be desirable to inhibit or suppress the immune system during a flare-up, but not long term, which could result in the patient becoming overly sensitive to an infection.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100 T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

In another aspect, the RNA construct can be delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Chimeric Antigen Receptor

The present invention provides a composition comprising a chimeric antigen receptor (CAR) or nucleic acid molecule encoding a CAR, wherein the CAR comprises a TACA-binding domain. In one embodiment, the CAR comprises an extracellular and intracellular domain. The extracellular domain comprises a target-specific binding element otherwise referred to as an antigen binding moiety. The intracellular domain or otherwise the cytoplasmic domain comprises, a costimulatory signaling region and a zeta chain portion. The costimulatory signaling region refers to a portion of the CAR comprising the intracellular domain of a costimulatory molecule. Costimulatory molecules are cell surface molecules other than antigens receptors or their ligands that are required for an efficient response of lymphocytes to antigen.

Between the extracellular domain and the transmembrane domain of the CAR, or between the cytoplasmic domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

Antigen Binding Moiety

In one embodiment, the CAR of the invention comprises a target-specific binding element otherwise referred to as an antigen binding moiety.

In one embodiment, the antigen binding moiety of the CAR of the present invention comprises one or more TACA-binding domains described elsewhere herein. For example, in one embodiment, the antigen binding moiety comprises one or more TACA-binding domains of any of SEQ ID NO: 1, SEQ ID NO: 2, SEQ ID NO; 3, SEQ ID NO: 4, SEQ ID NO: 5, SEQ ID NO: 6, SEQ ID NO: 7, or homologous peptides thereof.

In one embodiment, the composition comprises a nucleic acid molecule encoding a CAR, wherein the nucleic acid molecule comprises a nucleotide sequence that encodes any of SEQ ID NO: 1, SEQ ID NO: 2, SEQ ID NO; 3, SEQ ID NO: 4, SEQ ID NO: 5, SEQ ID NO: 6, SEQ ID NO: 7, or homologous peptides thereof.

In one embodiment, the antigen binding moiety of the CAR comprises a peptide that binds to a TACA-binding domain described herein. For example, in one embodiment, the antigen binding moiety of the CAR comprises a lectin-binding domain, wherein the lectin-binding domain binds to a lectin or lectin-derived peptide which binds to a TACA.

Transmembrane Domain

With respect to the transmembrane domain, the CAR can be designed to comprise a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Preferably, the transmembrane domain in the CAR of the invention is the CD8 transmembrane domain. In some instances, the transmembrane domain of the CAR of the invention comprises the CD8a hinge domain.

Cytoplasmic Domain

The cytoplasmic domain or otherwise the intracellular signaling domain of the CAR of the invention is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the invention comprises a cytoplasmic signaling sequence derived from CD3 zeta.

In a preferred embodiment, the cytoplasmic domain of the CAR can be designed to comprise the CD3-zeta signaling domain by itself or combined with any other desired cytoplasmic domain(s) useful in the context of the CAR of the invention. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, while the invention in exemplified primarily with 4-1BB as the co-stimulatory signaling element, other costimulatory elements are within the scope of the invention.

The cytoplasmic signaling sequences within the cytoplasmic signaling portion of the CAR of the invention may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the cytoplasmic domain is designed to comprise the signaling domain of CD3-zeta and the signaling domain of CD28. In another embodiment, the cytoplasmic domain is designed to comprise the signaling domain of CD3-zeta and the signaling domain of 4-1BB. In yet another embodiment, the cytoplasmic domain is designed to comprise the signaling domain of CD3-zeta and the signaling domain of CD28 and 4-1BB.'

Vectors

The present invention encompasses a nucleic acid molecule comprising sequences encoding a CAR, wherein the sequence comprises the nucleic acid sequence encoding an antigen binding moiety operably linked to the nucleic acid sequence encoding intracellular domain. For example, in one embodiment, the molecule encoding a CAR comprises a nucleic acid sequence encoding an antigen binding moiety comprising one or more TACA-binding domains of any of SEQ ID NO: 1, SEQ ID NO: 2, SEQ ID NO; 3, SEQ ID NO: 4, SEQ ID NO: 5, SEQ ID NO: 6, SEQ ID NO: 7, or homologous peptides thereof. In one embodiment, nucleic acid molecule encoding a CAR comprises a nucleic acid sequence comprising nucleotide sequence that encodes any of SEQ ID NO: 1, SEQ ID NO: 2, SEQ ID NO; 3, SEQ ID NO: 4, SEQ ID NO: 5, SEQ ID NO: 6, SEQ ID NO: 7, or homologous peptides thereof. In one embodiment, the nucleic acid molecule encoding a CAR comprises a nucleotide sequence that encodes a peptide that binds to a TACA-binding domain. For example, in one embodiment, the nucleic acid molecule encoding a CAR comprises a nucleotide sequence that binds to a lectin-binding domain, where the lectin-binding domain binds to a lectin or lectin-derived peptide that binds to a TACA.

The nucleic acid molecule may be any DNA or RNA construct, vector, or plasmid as described elsewhere herein.

Genetically Modified Cells

In certain embodiments, the composition of the invention comprises a cell modified to express a peptide of the invention. For example, in certain embodiments, the cell is modified to express a peptide comprising a TACA-binding domain. In certain embodiments, the cell is modified to express a peptide comprising a TACA-binding domain and a T-cell-binding domain. In certain embodiments, the cell is modified to express a CAR comprising a TACA-binding domain.

In certain embodiments, the cell is genetically modified by contacting the cell with an isolated nucleic acid encoding a peptide of the invention.

In some embodiments, the nucleic acid sequence is delivered into cells using a retroviral or lentiviral vector. For example, retroviral and lentiviral vectors expressing a peptide of the invention can be delivered into different types of eukaryotic cells as well as into tissues and whole organisms using transduced cells as carriers or cell-free local or systemic delivery of encapsulated, bound or naked vectors. The method used can be for any purpose where stable expression is required or sufficient.

In other embodiments, the nucleic acid sequence is delivered into cells using in vitro transcribed mRNA. In vitro transcribed mRNA can be delivered into different types of eukaryotic cells as well as into tissues and whole organisms using transfected cells as carriers or cell-free local or systemic delivery of encapsulated, bound or naked mRNA. The method used can be for any purpose where transient expression is required or sufficient.

In certain embodiments, the cell may be of any suitable cell type that can express the desired peptide. In certain embodiments, the modified cell is used in a method where the cell is introduced into a recipient. In certain embodiments, the cell is autologous, allogeneic, syngeneic or xenogeneic with respect to recipient.

In one embodiment, the cell is a T cell. The disclosed compositions and methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

Prior to expansion and genetic modification of the T cells of the invention, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than CD8$^+$ T cells in dilute concentrations. In one embodiment, the concentration of cells used is 5×10$^6$/ml. In other embodiments, the concentration used can be from about 1×10$^5$/ml to 1×10$^5$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaC, 10% Dextran 40 and 5% Dextrose, 20% Human Serum Albumin, and 7.5% DMSO or other suitable cell freezing media containing for example, Hespan and PlasmaLyte A, the cells then are frozen to –80° C. at a rate of 1 per minute and stored in the vapor phase of a liquid nitrogen storage tank. Other methods of controlled freezing may be used as well as uncontrolled freezing immediately at –20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Whether prior to or after genetic modification of the T cells to express a peptide of the invention, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4$^+$ T cells or CD8$^+$ T cells, an anti-CD3 antibody and an anti-CD28 antibody. Examples of an anti-CD28 antibody include 9.3, B-T3, XR-CD28 (Diaclone, Besangon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/m can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, CD4*) that is greater than the cytotoxic or suppressor T cell population ($T_C$, CD8+). E vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Scaffolds

The present invention provides a scaffold or substrate composition comprising a peptide comprising a TACA-binding domain, a nucleic acid molecule encoding a peptide comprising a TACA-binding domain, a cell modified to express a peptide comprising a TACA-binding domain, or a combination thereof. For example, in one embodiment, a peptide comprising a TACA-binding domain, a nucleic acid molecule encoding a peptide comprising a TACA-binding domain, a cell modified to express a peptide comprising a TACA-binding domain, or a combination thereof is present within a scaffold. In another embodiment, a peptide comprising a TACA-binding domain, a nucleic acid molecule encoding a peptide comprising a TACA-binding domain, a cell modified to express a peptide comprising a TACA-binding domain, or a combination thereof is applied to the surface of a scaffold. The scaffold of the invention may be of any type known in the art. Non-limiting examples of such a scaffold includes a, hydrogel, electrospun scaffold, foam, mesh, sheet, patch, and sponge.

Pharmaceutical Compositions

The present invention also provides pharmaceutical compositions comprising one or more of the compositions described herein. Formulations may be employed in admixtures with conventional excipients, i.e., pharmaceutically acceptable organic or inorganic carrier substances suitable for administration to the wound or treatment site. The pharmaceutical compositions may be sterilized and if desired mixed with auxiliary agents, e.g., lubricants, preservatives, stabilizers, wetting agents, emulsifiers, salts for influencing osmotic pressure buffers, coloring, and/or aromatic substances and the like. They may also be combined where desired with other active agents, e.g., other analgesic agents.

Administration of the compositions of this invention may be carried out, for example, by parenteral, by intravenous, intratumoral, subcutaneous, intramuscular, or intraperitoneal injection, or by infusion or by any other acceptable systemic method.

As used herein, "additional ingredients" include, but are not limited to, one or more of the following: excipients; surface active agents; dispersing agents; inert diluents; granulating and disintegrating agents; binding agents; lubricating agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

In an embodiment, the composition includes an antioxidant and a chelating agent that inhibits the degradation of one or more components of the composition. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the peptide or other composition of the invention in an aqueous or oily vehicle. Aqueous vehicles include, for example, water, and isotonic saline. Oily vehicles include, for example, almond oil, oily esters, ethyl alcohol, vegetable oils such as *arachis*, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid.

Therapeutic Application

The present invention provides a method of treating or preventing cancer in a subject in need thereof. The method may be used to treat any cancer, including a hematological malignancy, a solid tumor, a primary or a metastasizing tumor.

In one embodiment, the method comprises contacting the subject with a composition of the invention. For example, in certain embodiments, the method comprises contacting the subject with a composition comprising a peptide comprising a TACA-binding domain, a nucleic acid molecule encoding a peptide comprising a TACA-binding domain, a cell modified to express a peptide comprising a TACA-binding domain, or a combination thereof. In one embodiment, the method comprises contacting the subject with a composition comprising peptide comprising a TACA-binding domain and a T-cell-binding domain, a nucleic acid molecule encoding a peptide comprising a TACA-binding domain and a T-cell-binding domain, a cell modified to express a peptide comprising a TACA-binding domain and a T-cell-binding domain, or a combination thereof.

The invention provides the use of a peptide comprising a TACA-binding domain to specifically bind to a tumor cell, via binding to a TACA present on the tumor cell. In certain embodiments, the peptide is used to recruit a T-cell, via binding of the T-cell-binding domain to the T-cell, to a tumor cell expressing a TACA. Thus, the present invention also provides a method for stimulating a T cell-mediated immune response to a target cell population or tissue in a mammal comprising the step of administering to the mammal a composition described herein.

In certain embodiments, the method comprises contacting the subject with a composition comprising a peptide that binds to a TACA-binding domain, a nucleic acid molecule encoding a peptide that binds to a TACA-binding domain, or a cell modified to express a peptide that binds to a TACA-binding domain. For example, in one embodiment, the method comprises contacting the subject with a composition comprising a peptide comprising a lectin-binding domain, a nucleic acid encoding a peptide comprising a lectin-binding domain, or a cell modified to express a peptide comprising a lectin-binding domain, where the lectin-binding domain binds to a lectin or lectin-derived peptide that binds to a TACA.

In one embodiment, the method comprises (1) administering a composition comprising a peptide that binds to the TACA-binding domain, a nucleic acid molecule encoding a peptide that binds to a TACA-binding domain, or a cell modified to express a peptide that binds to a TACA-binding domain; and (2) administering a composition comprising a TACA-binding domain or a nucleic acid molecule encoding a peptide comprising a TACA-binding domain. For example, in one embodiment, the method comprises administering a composition comprising a lectin or lectin-derived peptide that binds the TACA and administering a bispecific antibody that binds to the lectin or lectin-derived peptide. In one embodiment, the method comprises administering a cell genetically modified to express a CAR, wherein the CAR comprises an antigen binding moiety comprising a lectin-binding domain and administering a composition comprising a lectin or lectin-derived peptide that binds to a TACA, such that the CAR binds to the lectin or lectin-derived peptide which binds to the TACA. In certain instances, it may be advantageous to administer a TACA-binding lectin and a lectin-binding composition (e.g. T cell engineered to express an anti-lectin CAR). First, this method can have the ability to time limit the T cell response as the half-life of the lectin is much shorter than the engineered T cell. The engineered T cells may remain for years, but without the lectin, the T cells would be inactive, thereby allowing for easier targeting of solid cancers by limiting persistence of the response.

In one embodiment, the present invention includes a type of cellular therapy where T cells are genetically modified to express a peptide of the invention, and the cell is infused to a recipient in need thereof. In certain embodiments, the infused cell is able to kill tumor cells in the recipient. Unlike antibody therapies, the modified cells are able to replicate in vivo resulting in long-term persistence that can lead to sustained tumor control.

In one embodiment, the modified T cells of the invention can undergo robust in vivo T cell expansion and can persist for an extended amount of time. In another embodiment, the modified T cells of the invention evolve into specific memory T cells that can be reactivated to inhibit any additional tumor formation or growth. For example, modified T cells of the invention can undergo robust in vivo T cell expansion and persist at high levels for an extended amount of time in blood and bone marrow and form specific memory T cells.

Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

The compositions of the present invention may be administered either alone, or as a pharmaceutical composition in combination with diluents and/or with other components such as IL-2 or other cytokines or cell populations. Briefly, pharmaceutical compositions of the present invention may comprise a composition as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount," "an anti-tumor effective amount," "an tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject).

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the compositions of the present invention are administered to a patient by intradermal or subcutaneous injection. In another embodiment, the compositions of the present invention are administered by i.v. injection. In certain embodiments, the compositions of be injected directly into a tumor or lymph node.

In certain embodiments, the compositions are administered to a patient in conjunction with (e.g., before, simultaneously or following) any number of relevant treatment modalities, including but not limited to treatment with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

In certain embodiments, the composition of the invention is administered during surgical resection or debulking of a tumor or diseased tissue. For example, in subjects undergoing surgical treatment of diseased tissue or tumor, the composition may be administered to the site in order to further treat the tumor.

In one embodiment, the method comprises administering to the subject a scaffold comprising a peptide comprising a TACA-binding domain, a nucleic acid molecule encoding a peptide comprising a TACA-binding domain, a cell modified to express a peptide comprising a TACA-binding domain, or a combination thereof.

Subjects to which administration of the compositions and pharmaceutical compositions of the invention is contemplated include, but are not limited to, humans and other primates, mammals including commercially relevant mammals such as non-human primates, cattle, pigs, horses, sheep, cats, and dogs.

The dosage of the above treatments to be administered to a patient will vary with the precise nature of the condition being treated and the recipient of the treatment. The scaling of dosages for human administration can be performed according to art-accepted practices. Strategies for T cell dosing and scheduling have been discussed (Ertl et al, 2011, Cancer Res, 71:3175-81; Junghans, 2010, Journal of Translational Medicine, 8:55).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Glycan-Dependent T Cell Recruiter (GlyTR)

Malignant transformation of cells is near universally accompanied with aberrant changes of glycosylation on the cell surface (Kim and Varki, 1997, Glycoconj J, 14: 569-576). Indeed, alteration of cell surface glycosylation has been observed in all types of experimental and human cancers (Hakomori, 2002, PNAS USA, 99: 10231-10233), and these altered sugar structures are called tumor-associated carbohydrate antigens (TACAs) (Table 1). This tumor-specific property makes cell surface TACAs an excellent target antigen for production of monoclonal antibodies targeting many common cancers. However, despite decades of effort, specific antibodies with high-affinity against TACAs are not yet available due to difficulties in generating antibodies to carbohydrate antigens.

One way to address this issue is to utilize lectins, proteins that bind carbohydrates. Evolution has produced hundreds of different carbohydrate-binding proteins that are highly specific for many different carbohydrate moieties. Moreover, lectins from both plants and animals have been used extensively for decades and their binding properties are well understood.

Described herein is a class of chimeric proteins that are comprised of a carbohydrate binding domain from a lectin coupled to an antibody domain that will bind T cells and/or other cancer killing cells. This class of chimeric proteins are referred to herein as Glycan-dependent T cell Recruiter (GlyTR). GlyTR chimeric proteins are designed to target cancer specific carbohydrate antigens and lead to T cell mediated death. Examples of novel GlyTR molecules are listed in Table 2.

Figure 2:
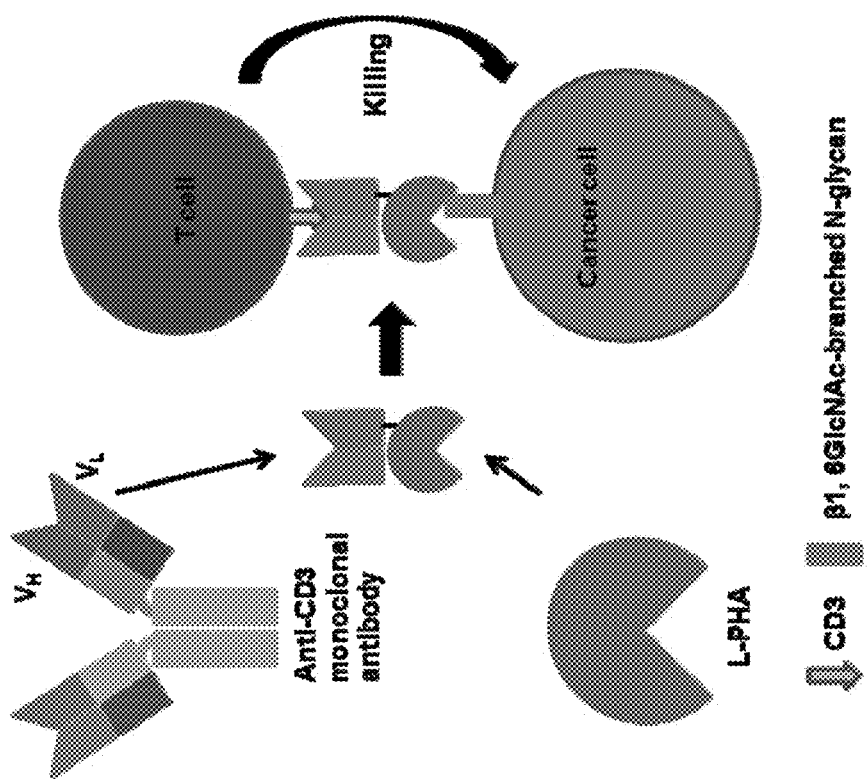
FIG. 2 is an illustration depicting the principle of L-PHA× CD3 chimeric protein. The chimeric protein is a single polypeptide chain comprising the variable heavy and light chains of anti-CD3 monoclonal antibody and the plant lectin L-PHA. It can engage a T cell and a cancer cell with β1, 6GcNAc-branched N-glycan. This interaction can activate the T cell and induce cytotoxic killing of the cancer cell.

To demonstrate the use of GlyTR molecules, a GlyTR was designed and produced that targets CD3 on T cells and β1,6 GcNAc-branched Asn (N) linked-glycans, a carbohydrate structure that is frequently over-expressed on many different types of cancer cells, including epithelial and hematopoietic cancers.

β1,6GcNAc-branched N-glycans are tri- and tetra-antennary oligosaccharides that constitute a subset of the complex-type N-glycans (FIG. 1). A highly specific plant lectin L-PHA (*Phaseolus vudgaris, leukoagglulinin*) has been used to measure β1,6GlcNAc-branching level of cells. To exploit the highly specific binding property of L-PHA to β1,6GlcNAc-branched N-glycans and the technology of bispecific antibody, a novel bispecific chimeric protein was created by generating a single chain polypeptide composed of both the lectin L-PHA and the scFv of anti-CD3 (L-PHA× CD3, FIG. 2).

Figure 3:
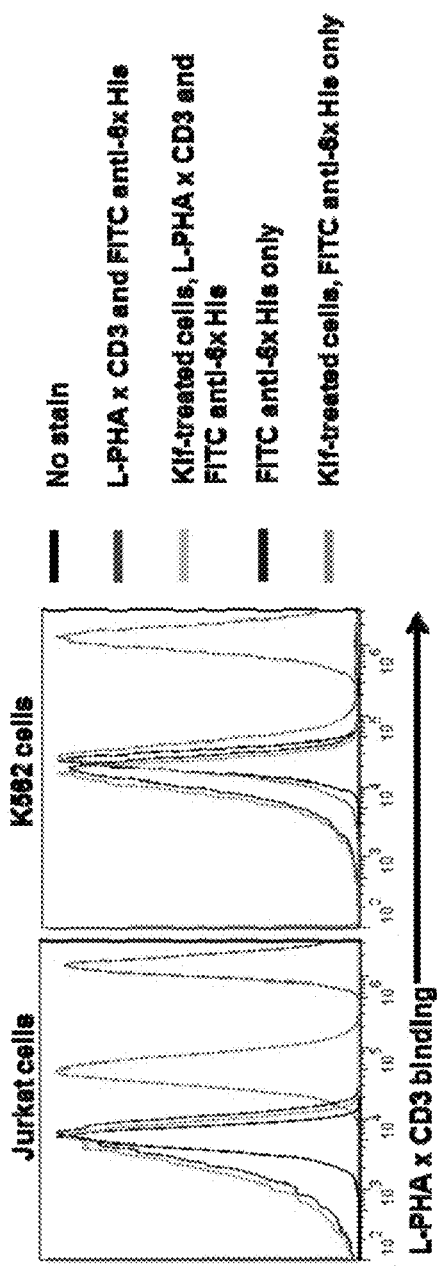
FIG. 3 depicts the results of an example experiment demonstrating that GlyTR L-PHA×CD3 binds both CD3 and tetra-antennary branched N-glycan. Flow cytometry analysis of cell surface L-PHA×CD3 binding on Jurkat (left) and K562 (right) cells with and without 3 days of pre-treatment with 10 µM Kifunensine (Kif). On Jurkat cells (left), L-PHA×CD3 was capable to bind both CD3 and tetra-antennary branched N-glycan, and binding was reduced if cells was pre-treated with Kif, which abrogated branching but left CD3 on the cell surface for binding. On CD3-negative chronic myelogenous leukemia cancer cell, K562 (right), binding was detected but not on Kif-treated K562 cells.

Flow cytometric analysis confirmed that GlyTR L-PHA× CD3 specifically binds β1,6GlcNAc-branched N-glycans, as demonstrated by complete reversal of binding to K562, a chronic myelogenous leukemia cell line, when the cells were pre-treated with the Golgi branching inhibitor kifunensine (FIG. 3). Binding to CD3 was also confirmed by analysis of Jurkat T cells expressing CD3 and treated with kifunensine, where treatment eliminated binding to 1,6GcNAc-branched N-glycans (FIG. 3).

Figures 4A, 4B, 4C, 4D, 4E, 4F, 4G, 4H, 4I, 4J:
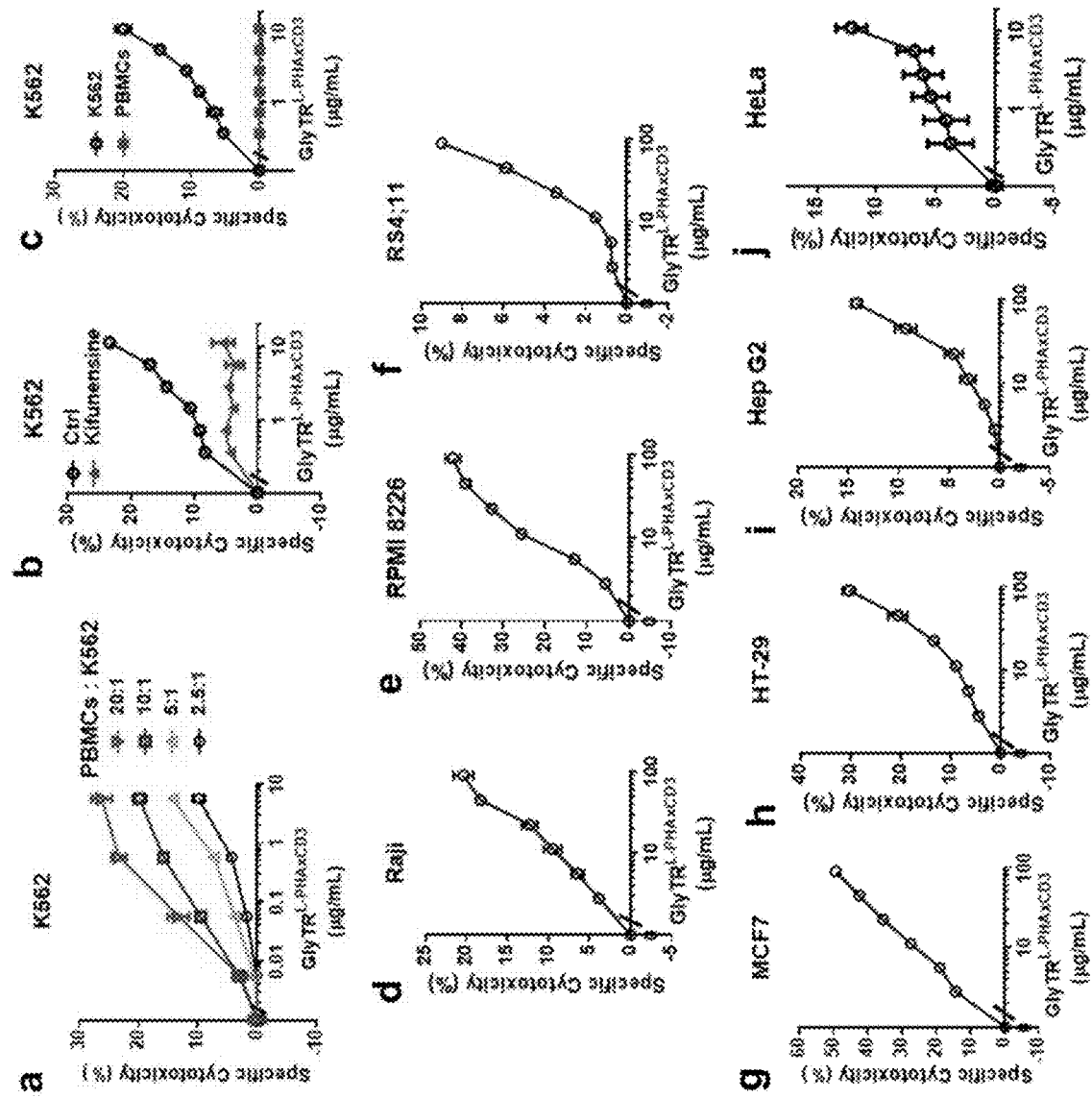
FIG. 4A through FIG. 4J, depicts the results of an example experiment demonstrating that GlyTR L-PHA×CD3 mediates killing of cancer cells. CFSE-labeled K562 (FIG. 4A-FIG. 4C), Kifunensine-treated K562 (FIG. 4B), Raji (FIG. 4D), RPMI 8226 (FIG. 4E), RS4;11 (FIG. 4F), MCF7 (FIG. 4G), HT-29 (FIG. 4H), Hep G2 (FIG. 4I), or HeLa (FIG. 4J) were seeded in 96-well plates. Human resting PBMCs and serial dilutions of GlyTR L-PHA×CD3 were added to the plate and incubated for 4 hours in a 37° C., 5% $CO_2$ incubator. Cytotoxicity was detected by propidium iodine (PI) (FIG. 4A-FIG. 4C, FIG. 4J) or 7AAD (FIG. 4D-FIG. 4I) staining and analyzed by flow cytometry. Specific cytotoxicity %=$CFSE^+PI^+\%_{oGlyTR}-CFSE^+PI^+\%_{non-treated}$ (FIG. 4A-FIG. 4C, FIG. 4J) or =$CFSE^+7-AAD^+\%_{GlyTR}-CFSE^+7-AAD^+\%_{non-treated}$ (FIG. 4D-FIG. 4I) and $CFSE-PI^+$ cells were gated for cytotoxicity analysis for PBMCs (FIG. 4C).
Figure 5:
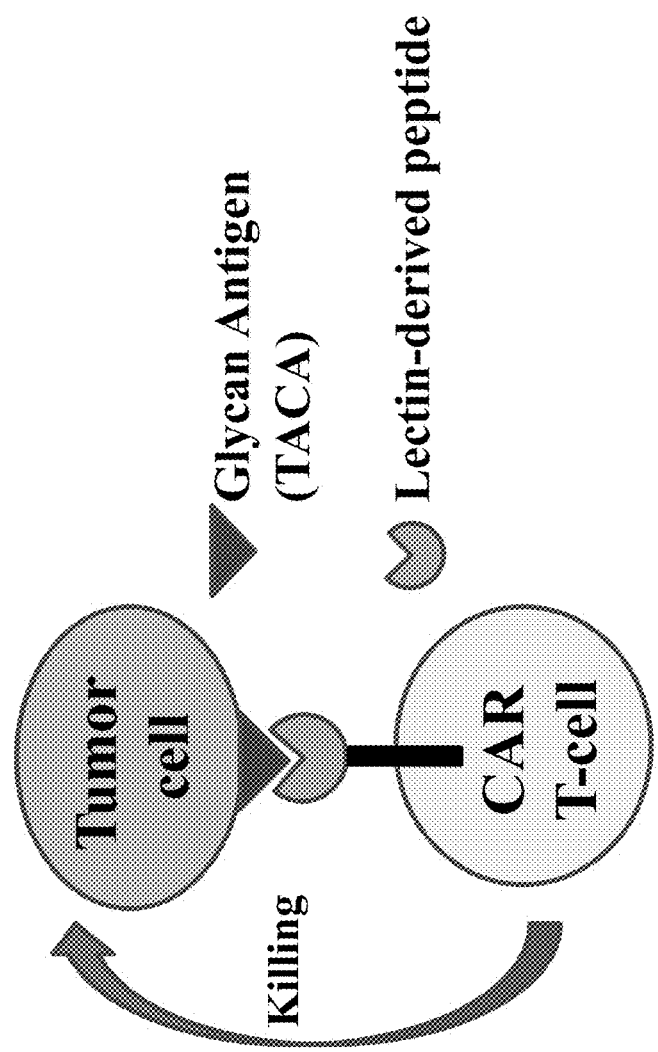
FIG. 5 is a schematic illustrating of an exemplary embodiment of the invention, where a T-cell is modified to express a chimeric antigen receptor (CAR) comprising a lectin-derived peptide that comprises a TACA-binding domain which binds to a TACA expressed on the tumor cell.
Figure 6:
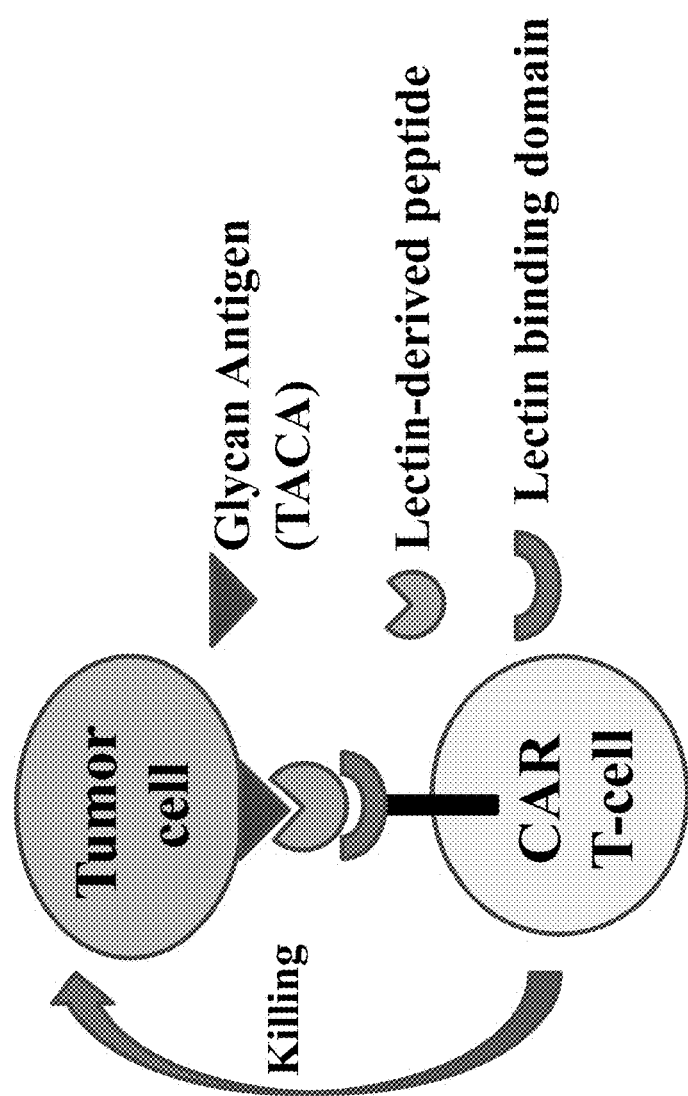
FIG. 6 is a schematic illustrating of an exemplary embodiment of the invention, where a T-cell is modified to express a chimeric antigen receptor (CAR) comprising a lectin binding domain. The lectin binding domain can bind to a lectin-derived peptide that comprises a TACA-binding domain which binds to a TACA expressed on the tumor cell.

GlyTR L-PHA×CD3 was tested for its ability to direct T cell killing against K562, B cell lymphoma (Raji), Multiple myeloma (RPMI 8226), Acute lymphoblastic leukemia (RS4;11), Breast adenocarcinoma (MCF7), Colorectal adenocarcinoma (HT-29), Liver hepatocellular carcinoma (Hep G2) and Cervical cancer (HeLa) cells using resting human peripheral blood mononuclear cells (PBMCs) as the effector cells in an antibody-dependent cell-mediated cytotoxicity (ADCC) assay (FIG. 4A-FIG. 4J). The results demonstrate that GlyTR L-PHA×CD3 dose-dependently induced T cell killing of cancer cells. Importantly, killing of cancer cells that had been pre-treated with the Golgi inhibitor Kifunensine to reduce β1,6GcNAc-branching was severely suppressed (FIG. 4B), demonstrating that killing induced by GlyTR L-PHA×CD3 is dependent on the presence of the carbohydrate antigen. Moreover, killing of off target (non-cancer) PBMCs was extremely low, demonstrating specificity to cancer (FIG. 4C).

In summary, GlyTR chimeric proteins provide an opportunity for the development of a novel class of therapeutic drugs for cancer immunotherapy, with significant advantages over existing technology. Based on the GlyTR concept and the availability of many different lectins specific for many different TACAs, multiple GlyTRs can be generated by replacing L-PHA with other lectins; or chimeric proteins we can be produced composed of lectins and scFv that can recruit other immune effector cells.

The functionality of the lectin domain can be improved through mutation. For example, GlyTR L-PHA×CD3 can be further improved by exchanging the carbohydrate binding domain of E-PHA with L-PHA, which increases binding ~20-30 fold (Kaneda et al., 2002, J Biol Chem, 277: 16928-16935). GlyTR L-PHA×CD3 appears to be a dimer and if this proves problematic, the first 5 N-terminal amino acids of L-PHA domain, which mediate dimer formation, can be deleted in the GlyTR L-PHA×CD3 protein to prevent dimerization. Finally, in addition to generating bispecific chimeric protein, lectins may be utilized in chimeric antigen receptor therapy for cancer (Barrett et al., 2014, Ann Rev Med, 65: 333-347).

Example 2: Amino Acid and Nucleotide Sequences

GlyTR L-PHA×CD3
Leader sequence—L-PHA-Linker-anti-CD3 scFv-His tag
Protein sequence: 525 aa (SEQ ID NO: 11)
MGWSCIILFLVATATGVHSSNDIYFNFQRFNETNLILQRDASVSSSGQLR
LTNLNGNGEPRVGSLGRAFYSAPIQIWDNTTGTVASFATSFTFNIQVPNN
AGPADGLAFALVPVGSQPKDKGGFLGLFDGSNSNFHTVAVEFDTLYNKDW
DPTERHIGIDVNSIRSIKTTRWDFVNGENAEVLITYDSSTNLLVASLVYP
SQKTSFIVSDTVDLKSVLPEWVSVGFSATTGINKGNVETNDVLSWSFASK
LSDGTTSEGLNLANLVLNKILGGGGSDIKLQQSGAELARPGASVKMSCKT
SGYTFTRYTMHWVKQRPGQGLEWIGYINPSRGYTNYNQKFKDKATLTTDK
SSSTAYMQLSSLTSEDSAVYYCARYYDDHYCLDYWGQGTTLTVSSVEGGS
GGSGGSGGSGGVDDIQLTQSPAIMSASPGEKVTMTCRASSSVSYMNWYQQ
KSGTSPKRWIYDTSKVASGVPYRFSGSGSGTSYSLTISSMEAEDAATYYC
QQWSSNPLTFGAGTKLELKHHHHHH.

Mutated GlyTR L-PHA×CD3, to monomerize the molecule.
Leader sequence—L-PHA$_{(\Delta 1-5)}$-Linker-anti-CD3 scFv-His tag
Protein sequence: 520 aa (SEQ ID NO: 12)
MGWSCIILFLVATATGVHSFNFQRFNETNLILQRDASVSSSGQLRLTNLN
GNGEPRVGSLGRAFYSAPIQIWDNTTGTVASFATSFTFNIQVPNNAGPAD
GLAFALVPVGSQPKDKGGFLGLFDGSNSNFHTVAVEFDTLYNKDWDPTER
HIGIDVNSIRSIKTTRWDFVNGENAEVLITYDSSTNLLVASLVYPSQKTS
FIVSDTVDLKSVLPEWVSVGFSATTGINKGNVETNDVLSWSFASKLSDGT
TSEGLNLANLVLNKILGGGGSDIKLQQSGAELARPGASVKMSCKTSGYTF
TRYTMHWVKQRPGQGLEWIGYINPSRGYTNYNQKFKDKATLTTDKSSSTA
YMQLSSLTSEDSAVYYCARYYDDHYCLDYWGQGTTLTVSSVEGGSGGSGG
SGGSGGVDDIQLTQSPAIMSASPGEKVTMTCRASSSVSYMNWYQQKSGTS
PKRWIYDTSKVASGVPYRFSGSGSGTSYSLTISSMEAEDAATYYCQQWSS
NPLTFGAGTKLELKHHHHHH Mutated GlyTR L-PHA×CD3, to increase binding affinity.
Leader sequence—Mutated L-PHA-Linker-anti-CD3 scFv-His tag
Protein sequence (SEQ ID NO: 13)
MGWSCIILFLVATATGVHSASQTSFSFQRFNETNLILQRDATVSSKGQLR
LTNVNDNGEPTLSSLGRAFYSAPIQIWDNTTGAVAASPTSFTFNIDVPNN
SGPADGLAFALVPVGSQPKDKGGFLGLFDGSNSNFHTVAVEFDTLYNKDW
DPKPRHIGIDVNSIKSIKTTTWDFVKGENAEVLITYDSSTKLLVASLVYP
SLKTSFIVSDTVDLKSVLPEWVIVGFTATTGITKGNVETNDILSWSFASK
LSDGTTSEALNLANFALNQILGGGGSDIKLQQSGAELARPGASVKMSCKT -continued SGYTFTRYTMHWVKQRPGQGLEWIGYINPSRGYTNYNQKFKDKATLTTDK
SSSTAYMQLSSLTSEDSAVYYCARYYDDHYCLDYWGQGTTLTVSSVEGGS
GGSGGSGGSGGVDDIQLTQSPAIMSASPGEKVTMTCRASSSVSYMNWYQQ
KSGTSPKRWIYDTSKVASGVPYRFSGSGSGTSYSLTISSMEAEDAATYYC
QQWSSNPLTFGAGTKLELKHHHHHH Mutated GlyTR L-PHA×CD3, to monomerize the molecule and to increase binding affinity.
Leader sequence—Mutated L-PHA-Linker-anti-CD3 scFv-His tag
Protein sequence (SEQ ID NO: 14)
MGWSCIILFLVATATGVHSFSFQRFNETNLILQRDATVSSKGQLRLTNVN
DNGEPTLSSLGRAFYSAPIQIWDNTTGAVAASPTSFTFNIDVPNNSGPAD
GLAFALVPVGSQPKDKGGFLGLFDGSNSNFHTVAVEFDTLYNKDWDPKPR
HIGIDVNSIKSIKTTTWDFVKGENAEVLITYDSSTKLLVASLVYPSLKTS
FIVSDTVDLKSVLPEWVIVGFTATTGITKGNVETNDILSWSFASKLSDGT
TSEALNLANFALNQILGGGGSDIKLQQSGAELARPGASVKMSCKTSGYTF
TRYTMHWVKQRPGQGLEWIGYINPSRGYTNYNQKFKDKATLTTDKSSSTA
YMQLSSLTSEDSAVYYCARYYDDHYCLDYWGQGTTLTVSSVEGGSGGSGG
SGGSGGVDDIQLTQSPAIMSASPGEKVTMTCRASSSVSYMNWYQQKSGTS
PKRWIYDTSKVASGVPYRFSGSGSGTSYSLTISSMEAEDAATYYCQQWSS
NPLTFGAGTKLELKHHHHHH

*Vicia villosa* isolectin B×CD3 scFv (VVAb×CD3)
VVA-Linker-CD3 scFV-His tag
Protein Sequence (SEQ ID NO: 15)
TESTSFSFTNFNPNQNNLILQEDALVNSAGTLELTAVAAGAPVPDSLGRA
LYAAPIHIHDNTTLASFTTSFSFVMAAPAAAAVADGLAFFLAPPDTQPQA
RGGFLGLFADRAHDASYQTVAVEFDTYSNAWDPNYTHIGIDTNGIESKKT
TPFDMVYGEKANIVITYQASTKALAASLVFPVSQTSYAVSARVDLRDILP
EYVRVGFSATTGLNAGVVETHDIVSWSFAVSLAGGGGSDIKLQQSGAELA
RPGASVKMSCKTSGYTFTRYTMHWVKQRPGQGLEWIGYINPSRGYTNYNQ
KFKDKATLTTDKSSSTAYMQLSSLTSEDSAVYYCARYYDDHYCLDYWGQG
TTLTVSSVEGGSGGSGGSGGSGGVDDIQLTQSPAIMSASPGEKVTMTCRA
SSSVSYMNWYQQKSGTSPKRWIYDTSKVASGVPYRFSGSGSGTSYSLTIS
SMEAEDAATYYCQQWSSNPLTFGAGTKLELKHHHHHH VVAb×CD3 (VVAb$_{\Delta 1\text{-}5}$×CD3 scFV)
VVAb$_{\Delta 1\text{-}5}$-Linker-CD3 scFV-His tag
Protein sequence (SEQ ID NO: 16)
FSFTNFNPNQNNLILQEDALVNSAGTLELTAVAAGAPVPDSLGRALYAAP
IHIHDNTTLASFTTSFSFVMAAPAAAAVADGLAFFLAPPDTQPQARGGFL
GLFADRAHDASYQTVAVEFDTYSNAWDPNYTHIGIDTNGIESKKTTPFDM VYGEKANIVITYQASTKALAASLVFPVSQTSYAVSARVDLRDILPEYVRV
GFSATTGLNAGVVETHDIVSWSFAVSLAGGGGSDIKLQQSGAELARPGAS
VKMSCKTSGYTFTRYTMHWVKQRPGQGLEWIGYINPSRGYTNYNQKFKDK
ATLTTDKSSSTAYMQLSSLTSEDSAVYYCARYYDDHYCLDYWGQGTTLTV
SSVEGGSGGSGGSGGSGGVDDIQLTQSPAIMSASPGEKVTMTCRASSSVS
YMNWYQQKSGTSPKRWIYDTSKVASGVPYRFSGSGSGTSYSLTISSMEAE
DAATYYCQQWSSNPLTFGAGTKLELKHHHHHH Extracellular Domain of CD301×CD3 scFv (CD301$_{EC}$×CD3)
CD301$_{EC}$-Linker-CD3 scFV-His tag
Protein Sequence (SEQ ID NO: 17)
QNSKFQRDLVTLRTDFSNFTSNTVAEIQALTSQGSSLEETIASLKAEVE
GFKQERQAGVSELQEHTTQKAHLGHCPHCPSVCVPVHSEMLLRVQQLVQ
DLKKLTCQVATLNNNASTEGTCCPVNWVEHQDSCYWFSHSGMSWAEAEK
YCQLKNAHLVVINSREEQNFVQKYLGSAYTWMGLSDPEGAWKWVDGTDY
ATGFQNWKPGQPDDWQGHGLGGGEDCAHFHPDGRWNDDVCQRPYHWVCE
AGLGQTSQESHGGGGSDIKLQQSGAELARPGASVKMSCKTSGYTFTRYT
MHWVKQRPGQGLEWIGYINPSRGYTNYNQKFKDKATLTTDKSSSTAYMQ
LSSLTSEDSAVYYCARYYDDHYCLDYWGQGTTLTVSSVEGGSGGSGGSG
GSGGVDDIQLTQSPAIMSASPGEKVTMTCRASSSVSYMNWYQQKSGTSP
KRWIYDTSKVASGVPYRFSGSGSGTSYSLTISSMEAEDAATYYCQQWSS
NPLTFGAGTKLELKHHHHHH GlyTR L-PHA× CD3
Gene sequence: 1604 bp (Codon optimization with both 293 and CHO)
EcoRI-Kozak sequence—Leader sequence—L-PHA-Linker-anti-CD3 scFv-His tag—XbaI
EcoRI and XbaI sequences are underlined. Kozak sequence is bold.

(SEQ ID NO: 18)
GAATTCCCGCCGCCACCATGGGTTGGTCTTGCATCATCCTGTTCCTGGTCGCCACTG
CTACTGGGGTCCACTCTTCTAACGACATCTACTTTAACTTTCAGCGTTTCAATGAGAC
AAACCTGATCCTGCAGAGGGACGCCAGCGTGTCCAGCTCTGGCCAGCTGCGGCTGAC
CAACCTGAATGGCAACGGAGAGCCAAGGGTGGGCTCCCTGGGACGGGCCTTCTATTC
CGCCCCATCCAGATCTGGGACAATACCACAGGCACAGTGGCCTCCTTCGCCACCTC
CTTCACCTTCAACATCCAAGTGCCCAACAATGCCGGCCCTGCTGATGGCCTGGCCTTC
GCTCTGGTGCCAGTGGGCTCTCAGCCCAAGGACAAGGGCGGCTTCCTGGGCCTCTTT
GATGGCAGCAATTCTAACTTCCACACCGTGGCTGTGGAGTTTGACACACTGTACAAT
AAGGACTGGGACCCCACCGAGAGGCATATCGGCATCGACGTGAACTCCATCAGAAG
CATCAAGACCACAAGATGGATTTTGTGAATGGCGAGAACGCCGAGGTCCTGATCAC
CTATGATTCCAGCACAAACCTGCTGGTGGCTAGCCTGGTGTACCCCTCTCAGAAGAC
CTCCTTCATCGTGAGCGATACAGTGGATCTGAAGTCTGTGCTGCCTGAGTGGGTGTCT
GTGGGCTTTTCCGCCACCACCGGCATCAATAAGGGCAACGTGGAGACCAATGACGTG
CTGTCCTGGAGCTTTGCCTCTAAGCTGTCCGATGGCACCACATCTGAGGGCCTGAATC
TGGCTAACCTGGTGCTGAACAAGATCCTGGGCGGCGGCGGCTCTGACATCAAGCTGC
AGCAGTCCGGAGCTGAGCTGGCTAGGCCTGGAGCTAGCGTGAAGATGTCTTGCAAG
ACCTCCGGCTACACCTTCACAAGGTATACAATGCACTGGGTCAAGCAGAGACCCGGC
CAGGGCCTGGAGTGGATCGGCTATATCAATCCTTCCCGGGGCTATACCAATTATAAC
CAGAAGTTTAAGGACAAGGCCACCCTGACCACCGATAAGTCTTCCAGCACAGCTTAT
ATGCAGCTGTCTTCCCTGACCAGCGAGGACTCTGCCGTGTACTATTGCGCTAGGTACT
ATGACGATCATTACTGTCTGGATTATTGGGGCCAAGGCACCACACTGACAGTGAGCT
CTGTGGAGGGAGGCTCCGGAGGCAGCGGAGGCTCTGGAGGCTCCGGAGGAGTGGAC
GACATCCAGCTGACCCAGTCCCCTGCCATCATGTCTGCTTCCCCCGGCGAGAAGGTC
ACCATGACATGCAGGGCCTCCAGCTCTGTGAGCTACATGAACTGGTATCAGCAGAAG
AGCGGCACATCTCCTAAGAGATGGATCTACGACACCAGCAAGGTGGCCTCTGGCGTG

```
                         -continued
CCATATAGGTTCAGCGGCTCTGGCTCCGGCACCAGCTACTCTCTGACAATCTCCAGC

ATGGAGGCTGAGGATGCCGCTACCTACTATTGTCAGCAGTGGTCTTCCAATCCTCTG

ACATTTGGGGCTGGGACTAAACTGGAACTGAAACACCACCACCACCACCACTGATAA tctaga
```

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising at least one selected from the group consisting of:
   a) a peptide comprising a tumor-associated carbohydrate antigen (TACA)-binding domain derived from a lectin, and an immune cell recognition domain that specifically binds to a receptor on an immune effector cell; and
   b) an isolated nucleic acid molecule encoding a peptide, wherein the peptide comprises a TACA-binding domain derived from a lectin, and an immune cell recognition domain that specifically binds to a receptor on an immune effector cell,
   wherein the TACA-binding domain specifically binds to a TACA of a tumor cell,
   wherein:
      the lectin is selected from the group consisting of a galectin, a siglec, a selectin; a C-type lectin; CD301, L-PHA (*Phaseolus vulgaris* leukoagglutinin); E-PHA (*Phaseolus vulgaris* erythroagglutinen); tomato lectin (*Lycopersicon esculentum* lectin; LEA); peanut lectin (*Arachis hypogaea* Agglutinin; PNA); potato lectin (*Solanum tuberosum* lectin), pokeweed mitogen (*Phytolacca* American lectin), wheat germ agglutinin (*Triticum* Vulgaris lectin); *Artocarpus polyphemus* lectin (Jacalin letin); *Vicia villosa* Agglutinin (VVA); *Helix pomatia* Agglutinin (HPA); *Wisteria floribunda* Agglutinin (WFA); *Sambucus nigra* Agglutinin (SNA), BC2L-CNt (lectin from the gram negative bacteria *Burkholderia cenocepacia*), *Maackia amurensis* leukoagglutinin (MAL), *Psathyrella velutina* (PVL), *Sclerotium rolfsii* lectin (SRL), *Eucheuma serra* agglutinin (ESA), CLEC17A (Prolectin), *Aleuria aurantia* lectin, *Sambucus sieboldiana* lectin (SSA), *Glechoma hederacea* lectin (Gleheda), *Morus nigra* agglutinin (Morniga G), *Salvia sclarea* lectin, *Salvia* bogotensis lectin, *Salvia* horminum lectin, *Clerodendrum trichotomum* lectin, *Moluccella laevis* lectin, *Griffonia simplicifolia* (GsLA4), *Psophocarpus tetragonolobus* (acidic WBAI), *Abrus precatorius* lectin, *Amaranthus caudatus* lectin, *Amaranthus* leucocarpus lectin, Laelia *autumnalis* lectin, *Artocarpus integrifolia* lectin, *Maclura pomifera* lectin, *Artocarpus lakoocha* lectin, *Dolichos biflorus* agglutinin, *Dolichos biflorus* lectin, *Glycine max* lectin, and *Agaricus bisporus* lectin;
   wherein the immune effector cell is selected from the group consisting of T cells, natural killer (NK) cells, natural killer T (NKT) cells, macrophages, monocytes, dendritic cells, and neutrophils.

2. The composition of claim 1, wherein the galectin is selected from the group consisting of galectin-1, galectin-2, galectin-3, galectin-4, galectin-5, galectin-6, galectin-7, galectin-8, galectin-9, galectin-10, galectin-11, galectin-12, galectin-13, galectin-14 and galectin-15.

3. The composition of claim 1, wherein the siglec is selected from the group consisting of siglec-1 (sialoadhesion), siglec-2 (CD22), siglec-3 (CD33), siglec-4 (myelin associated glycoprotein), siglec-5, siglec-6, siglec-7, siglec-8, siglec-9, siglec-10, siglec-11, siglec-12, siglec-13, siglec-14, siglec-15, siglec-16, siglec-17, Siglec E, Siglec F, siglec G and siglec H.

4. The composition of claim 1, wherein the TACA-binding domain comprises an amino acid sequence selected from the group consisting of SEQ ID NO: 1, an amino acid sequence having greater than about 90% homology to SEQ ID NO: 1, SEQ ID NO: 2, an amino acid sequence having greater than about 90% homology to SEQ ID NO: 2, SEQ ID NO: 3, an amino acid sequence having greater than about 90% homology to SEQ ID NO: 3, SEQ ID NO: 4, an amino acid sequence having greater than about 90% homology to SEQ ID NO: 4, SEQ ID NO: 5, an amino acid sequence having greater than about 90% homology to SEQ ID NO: 5, SEQ ID NO: 6, an amino acid sequence having greater than about 90% homology to SEQ ID NO: 6, SEQ ID NO: 7, and an amino acid sequence having greater than about 90% homology to SEQ ID NO: 7.

5. The composition of claim 1, wherein the peptide is an Fc fusion peptide comprising the TACA-binding domain linked to an Fc domain.

6. The composition of claim 1, wherein the immune cell recognition domain that specifically binds to a receptor on an immune effector cell comprises a T-cell-binding domain, where the T-cell-binding domain specifically binds to a T-cell.

7. The composition of claim 6, wherein the T-cell-binding domain binds to at least one of the group consisting of CD3, T-cell receptor, CD2, CD28, and CD25.

8. The composition of claim 6, wherein the T-cell binding domain comprises an amino acid sequence selected from the group consisting of SEQ ID NO: 9 and an amino acid sequence having greater than about 90% homology to SEQ ID NO: 9.

9. The composition of claim 6, wherein the peptide comprises an amino acid sequence selected from the group consisting of SEQ ID NO: 11, an amino acid sequence having greater than about 90% homology to SEQ ID NO: 11, SEQ ID NO: 12, an amino acid sequence having greater than about 90% homology to SEQ ID NO: 12, SEQ ID NO: 13, an amino acid sequence having greater than about 90% homology to SEQ ID NO: 13, SEQ ID NO: 14, an amino acid sequence having greater than about 90% homology to SEQ ID NO: 14, SEQ ID NO: 15, an amino acid sequence having greater than about 90% homology to SEQ ID NO: 15, SEQ ID NO: 16, an amino acid sequence having greater than about 90% homology to SEQ ID NO: 16, SEQ ID NO: 17, and an amino acid sequence having greater than about 90% homology to SEQ ID NO: 17.

10. The composition of claim 1, wherein the immune cell recognition domain that specifically binds to a receptor on an immune effector cell comprises a NK-cell-binding domain, where the NK-cell-binding domain specifically binds to a NK-cell.

11. The composition of claim 10, wherein the NK-cell-binding domain binds to at least one of the group consisting of CD16 and NKG2D.

* * * * *

UNITED STATES PATENT AND TRADEMARK OFFICE
CERTIFICATE OF CORRECTION

| | | |
|---|---|---|
| PATENT NO. | : 10,925,972 B2 | Page 1 of 1 |
| APPLICATION NO. | : 15/571101 | |
| DATED | : February 23, 2021 | |
| INVENTOR(S) | : Demetriou et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 190 days.

Signed and Sealed this
Tenth Day of January, 2023

*Katherine Kelly Vidal*

Katherine Kelly Vidal
*Director of the United States Patent and Trademark Office*